US011672815B2

(12) United States Patent
Yang et al.

(10) Patent No.: US 11,672,815 B2
(45) Date of Patent: *Jun. 13, 2023

(54) COMPOSITION FOR INHIBITING IMMUNE CELL PROLIFERATION COMPRISING SIALYLLACTOSE OR DERIVATIVE THEREOF AND METHOD THEREOF

(71) Applicant: CUPIONE CO., LTD., Seoul (KR)

(72) Inventors: Siyoung Yang, Suwon-si (KR); Jimin Jeon, Daegu (KR); Li-Jung Kang, Busan (KR); Chanmi Cho, Jindo-gun (KR)

(73) Assignee: CUPIONE CO., LTD., Seoul (KR)

( * ) Notice: Subject to any disclaimer, the term of this patent is extended or adjusted under 35 U.S.C. 154(b) by 54 days.

This patent is subject to a terminal disclaimer.

(21) Appl. No.: 17/165,627

(22) Filed: Feb. 2, 2021

(65) Prior Publication Data

US 2021/0236525 A1  Aug. 5, 2021

Related U.S. Application Data

(60) Continuation of application No. 16/686,744, filed on Nov. 18, 2019, now abandoned, which is a division of application No. 16/130,522, filed on Sep. 13, 2018, now Pat. No. 11,291,676, which is a continuation-in-part of application No. PCT/KR2017/010489, filed on Sep. 22, 2017.

(30) Foreign Application Priority Data

Jan. 23, 2017 (KR) .................. 10-2017-0010540
May 31, 2017 (KR) .................. 10-2017-0067915

(51) Int. Cl.
A61K 31/702 (2006.01)
A23L 33/125 (2016.01)
A61P 17/00 (2006.01)
A61P 19/02 (2006.01)

(52) U.S. Cl.
CPC .......... *A61K 31/702* (2013.01); *A23L 33/125* (2016.08); *A61P 17/00* (2018.01); *A61P 19/02* (2018.01); *A23V 2002/00* (2013.01)

(58) Field of Classification Search
CPC ..... A61K 31/702; A23L 33/125; A61P 17/00; A61P 19/02; A23V 2002/00
USPC .......................................................... 514/54
See application file for complete search history.

(56) References Cited

U.S. PATENT DOCUMENTS

| 5,164,374 | A | 11/1992 | Rademacher et al. |
| 9,603,878 | B2 | 3/2017 | Berry et al. |
| 9,610,307 | B2 | 4/2017 | Berry et al. |
| 11,291,676 | B2 * | 4/2022 | Yang ................ A61P 19/02 |
| 2007/0286896 | A1 | 12/2007 | Yamazaki et al. |
| 2012/0071441 | A1 | 3/2012 | Tamerlani et al. |
| 2012/0202753 | A1 | 8/2012 | Morrow |
| 2012/0294946 | A1 | 11/2012 | Scott |
| 2013/0035481 | A1 | 2/2013 | Perez Figueroa et al. |
| 2016/0143961 | A1 | 5/2016 | Berry et al. |
| 2016/0143962 | A1 | 5/2016 | Berry et al. |
| 2016/0193258 | A1 | 7/2016 | Berry et al. |
| 2016/0199424 | A1 | 7/2016 | Berry et al. |
| 2016/0235792 | A1 | 8/2016 | Berry et al. |
| 2016/0271188 | A1 | 9/2016 | Berry et al. |

FOREIGN PATENT DOCUMENTS

| KR | 10-2014-0088805 A | 7/2014 |
| WO | WO 98/48817 A1 | 11/1998 |
| WO | 2005/011633 A1 | 2/2005 |
| WO | 2009/095240 A1 | 8/2009 |
| WO | WO 2010/116317 A1 | 10/2010 |
| WO | WO 2011/100979 A1 | 8/2011 |

OTHER PUBLICATIONS

Russo et al. Glycomics: New Challenges and Opportunities in Regenerative Medicine. Chem. Eur. J. 2016, 22, 13380-13388. (Year: 2016).*
International Search Report dated Jan. 30, 2018 in PCT/KR2017/010489 (with English translation), 5 pages.
Korean Office Action dated Apr. 19, 2017 in Patent Application No. 10-2017-0010540, 4 pages.
Korean Office Action dated Aug. 10, 2017 in Patent Application No. 10-2017-0010540, 2 pages.
Korean Office Action dated Aug. 17, 2017 in Patent Application No. 10-2017-0067915, 2 pages
Sgambato, A., et al., "Different Sialoside Epitopes on Collagen Film Surfaces Direct Mesenchymal Stem Cell Fate", ACS Applied Materials & Interfaces, vol. 8, No. 24, 2015, pp. 14952-14957.
Pelletier, J. P., et al, "Osteoarthritis, an Inflammatory Disease: Potential Implication for the Selection of New Therapeutic Targets" Arthritis & Rheumatism, vol. 44, No. 6. Jun. 2001, pp. 1237-1247.
Pritchard, M. H., et al., "Gold and Penicillamine: A Proposed Mode of Action in Rheumatoid Arthritis, Based on Synovial Fluid Analysis" Annals of the Rheumatic Diseases, vol. 37, 1978, pp. 493-503.
Peterson, L., et al., "Treatment of Osteochondritis Dissecans of the Knee with Autologous Chondrocyte Transplantation" The Journal of Bone and Joint Surgery, Incorporated, vol. 85-A, Supplement 2, 2003, pp. 17-24.
Izquierdo-Useros, N., et al., "Sialyllactose in Viral Membrane Gangliosides Is a Novel Molecular Recognition Pattern for Mature Dendritic Cell Capture of HIV-1" Plos Biology, vol. 10, Issue 4, Apr. 2012, pp. 1-15.

(Continued)

*Primary Examiner* — Yih-Horng Shiao
(74) *Attorney, Agent, or Firm* — Oblon, McClelland, Maier & Neustadt, L.L.P.

(57) ABSTRACT

Provided are a composition for inhibiting immune cell proliferation, including sialyllactose or a derivative thereof as an active ingredient, and a method of inhibiting immune cell proliferation, wherein the composition and the method may decrease expression of chemokines, decrease expression of pro-inflammatory cytokines, decrease production of inflammatory mediators, decrease expression of COX2, and decrease production of $PEG_2$, and therefore, may be useful for the prevention or treatment of atopic dermatitis or arthritis.

17 Claims, 34 Drawing Sheets

Specification includes a Sequence Listing.

(56) References Cited

OTHER PUBLICATIONS

Yusuf, E., et al., "Do Knee Abnormalities Visualised on MRI Explain Knee Pain in Knee Osteoarthritis? A Systematic Review" Ann Rheum Dis., vol. 70, 2011, pp. 60-67.
Berenbaum, F. "Osteoarthritis as an Inflammatory Disease (Osteoarthritis is not Osteoarthrosis!)" OARSI, Osteoarthritis Research Society International, vol. 21, 2013, pp. 16-21.
"Knee cartilage Repair Market-Competitive Landscape of Products" Frost & Sullivan, 2014, 1 page.
Abramson, S. B. "The Role of COX-2 Produced by Cartilage in Arthritis" Osteoarthritis and Cartilage vol. 7, No. 4, 1999, pp. 380-381.
Yoon, H. M., et al., "Stem Cell Therapy in Articular Cartilage Injury" Journal of Rheumatic Diseases, vol. 19. No. 3, Jun. 2012, pp. 125-131.
Park. K. W., et al., "In Vivo Cartilage Formation Using Human Bone Marrow-Derived Mesenchymal Stem Cells Mixed with Fibrin Glue" J. Korean Orthopaedic Research Society, vol. 18, No. 2, Dec. 2015, 1 page.
Mamidi, M. K., et al., "Mesenchymal Stromal Cells for Cartilage Repair in Osteoarthritis" OARSI, Osteoarthritis Research Society International, vol. 24, 2016, pp. 1307-1316.
Zhou, G., et al., "Three High Mobility Group-like Sequences within a 48-Base Pair Enhancer of the Col2a1 Gene Are Required for Cartilage-specific Expression in Vivo" The Journal of Biological Chemistry, vol. 273, No. 24, Jun. 12, 1998, pp. 14989-14997.
Yang, S., et al., "Hypoxia-inducible Factor-$2\alpha$ is a Catabolic Regulator of Osteoarthritic Cartilage Destruction" Nature Medicine, vol. 16, No. 6, Jun. 2010, pp. 687-694.
Glossary of medical education terms, Institute of International Medical Education, http://www.iime.org/glossary.htm Accessed in Mar. 2013. (Year: 2013) (Year: 2013).
Von Ristok LJ. Do artificial oligosaccharides in infant formula reduce the risk of atopic disease and allergies similar to human milk oligosaccharides? Thesis, BSc Biomedical Sciences Rijksuniversiteit Groningen. Jul. 28, 2012. (Year: 2012).
Extended European Search Report dated Nov. 16, 2020 in European Patent Application No. 17892942.8, 10 pages.
Ananthila Anandacoomarasamy, et al., "Current Evidence for Osteoarthritis Treatments" Therapeutic Advances in Musculoskeletal Disease, vol. 2, No. 1, Feb. 1, 2010, pp. 17-28.

\* cited by examiner

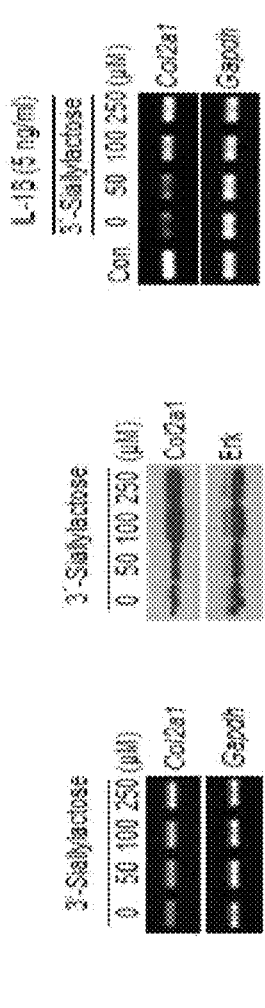
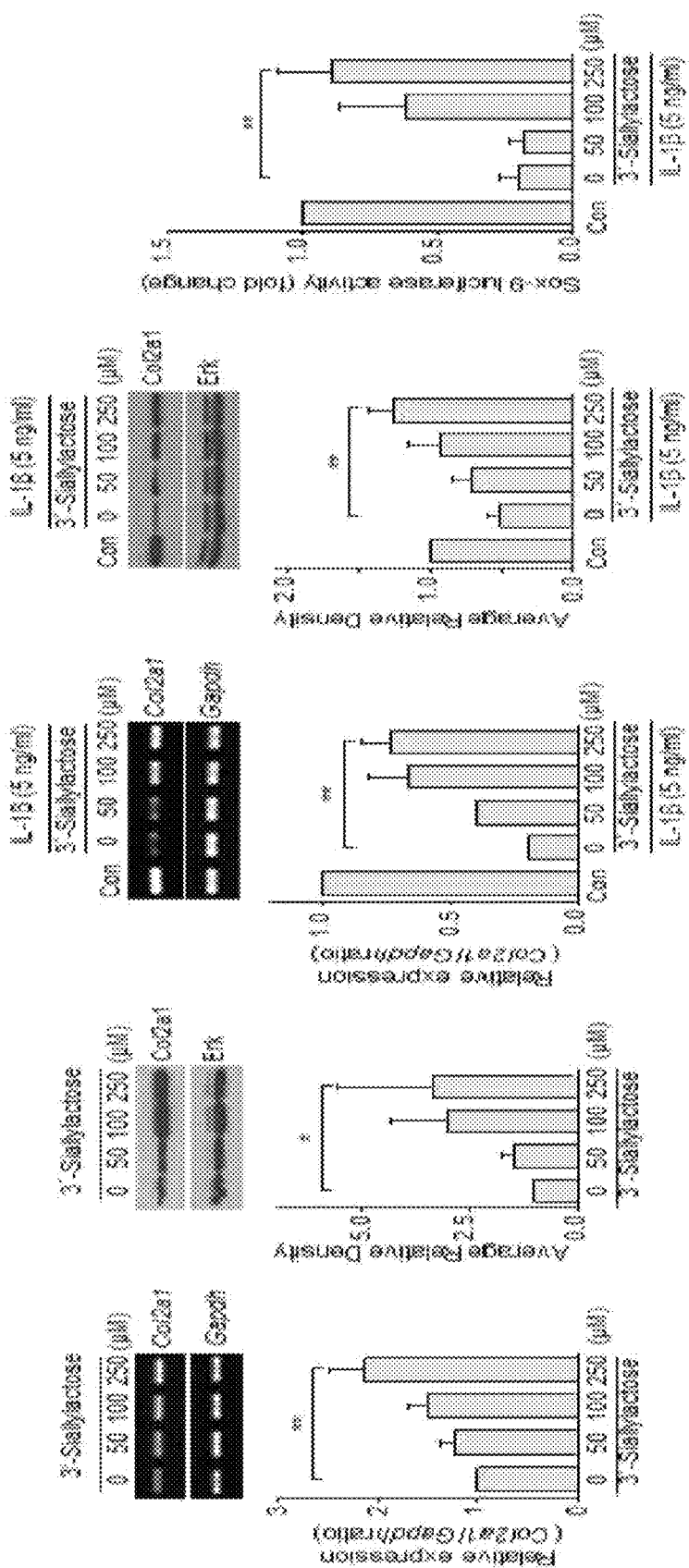
FIG. 4A FIG. 4B FIG. 4C FIG. 4D FIG. 4E

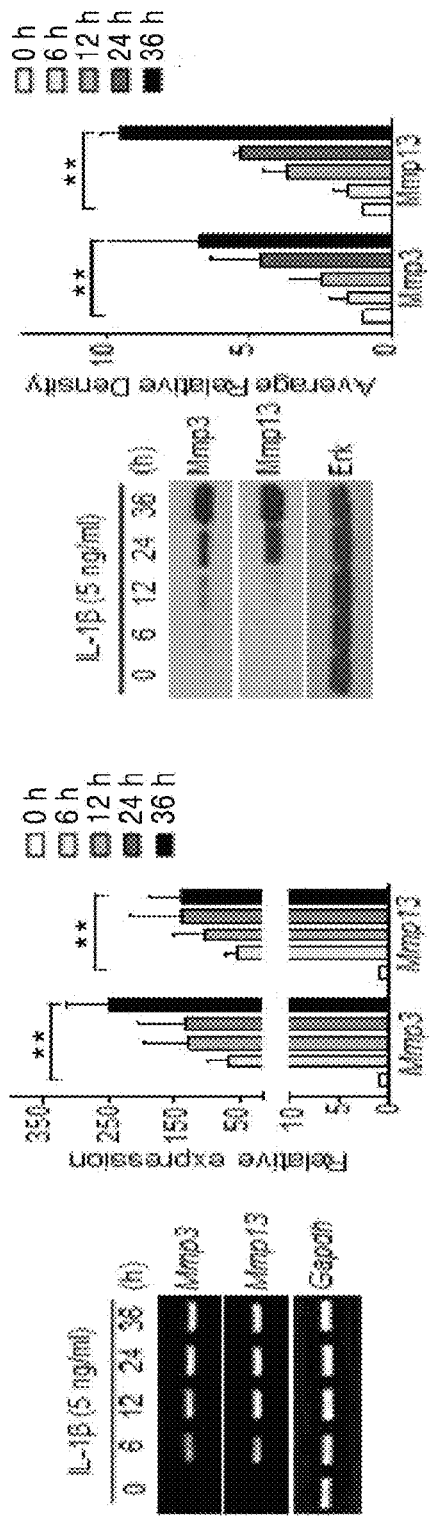
FIG. 6A
FIG. 6B
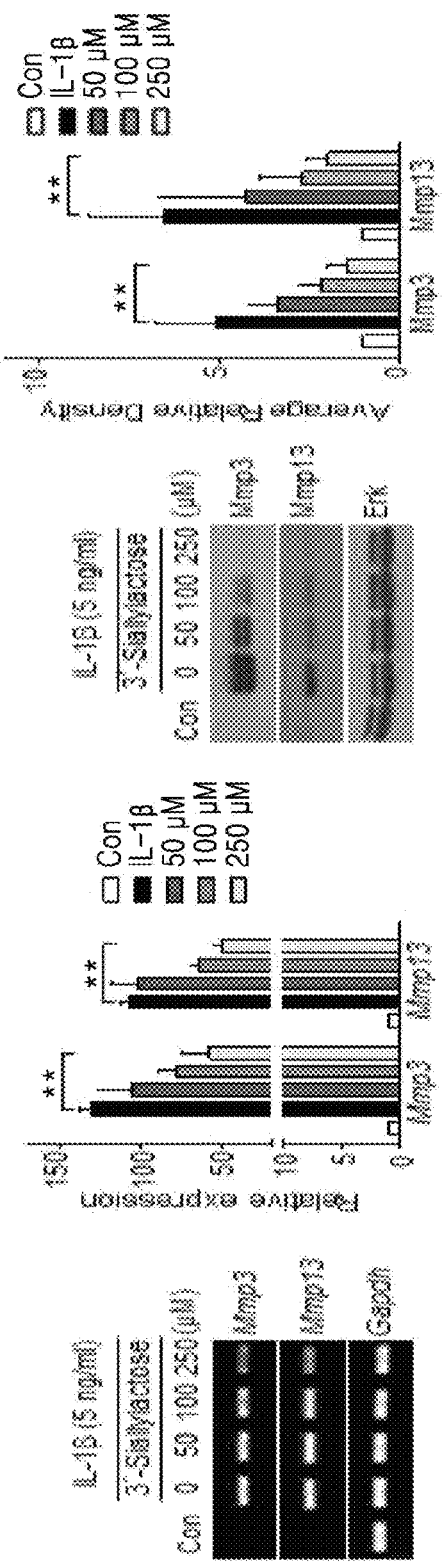
FIG. 6C
FIG. 6D

FIG. 13A
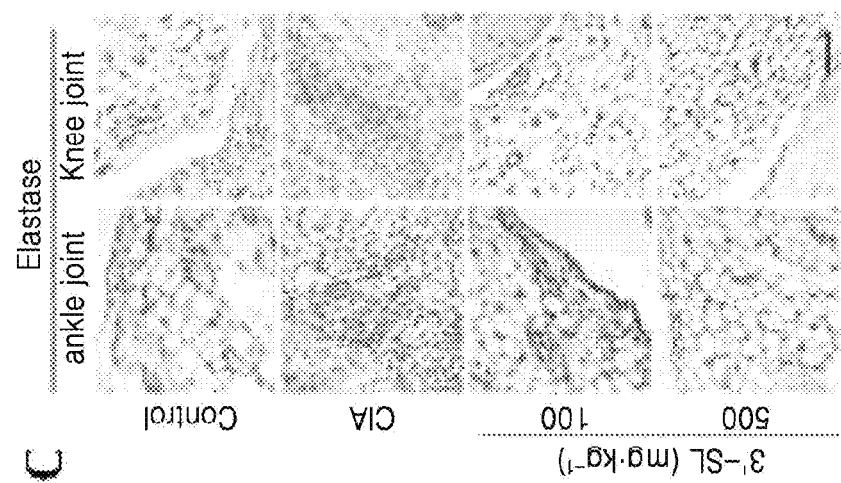
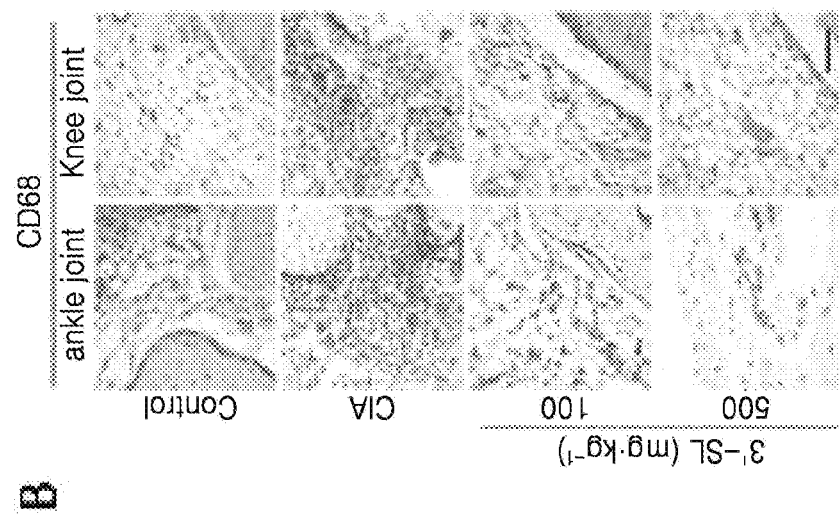
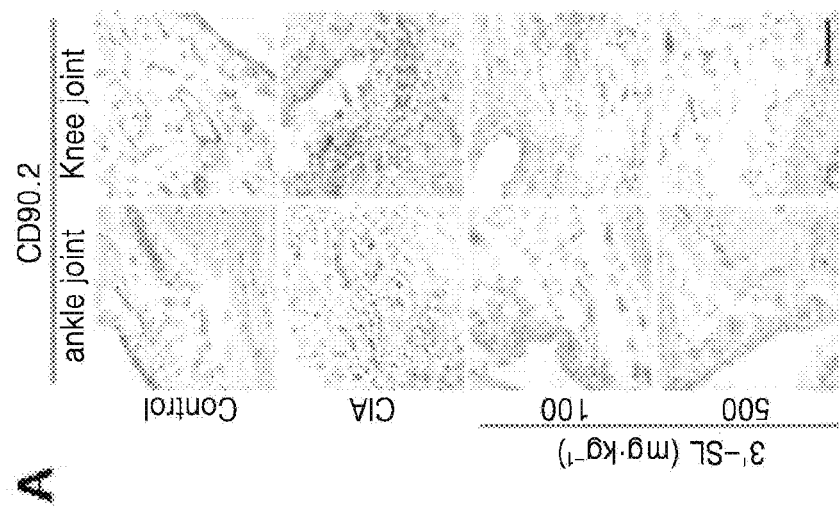

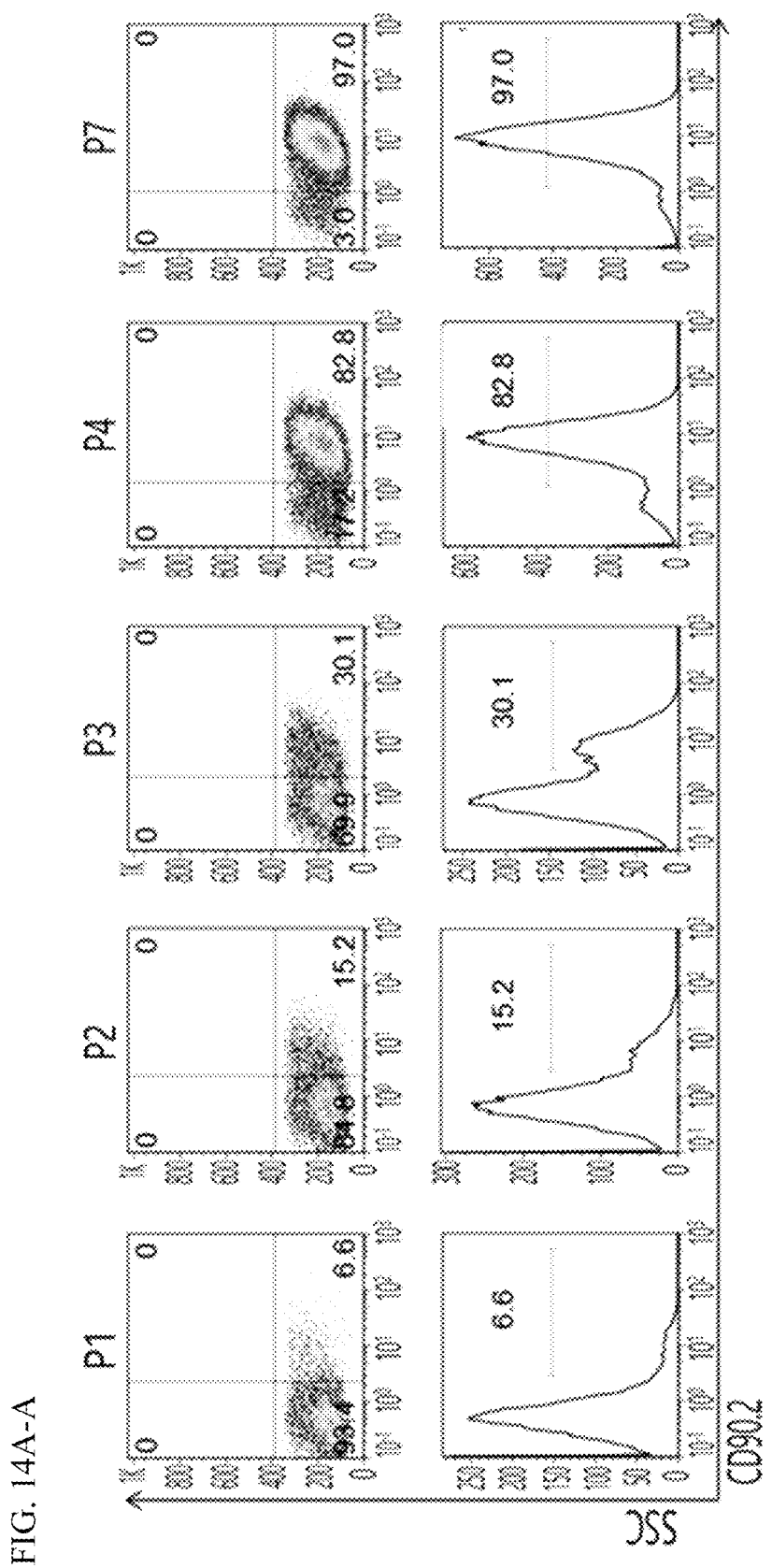
FIG. 14A-A

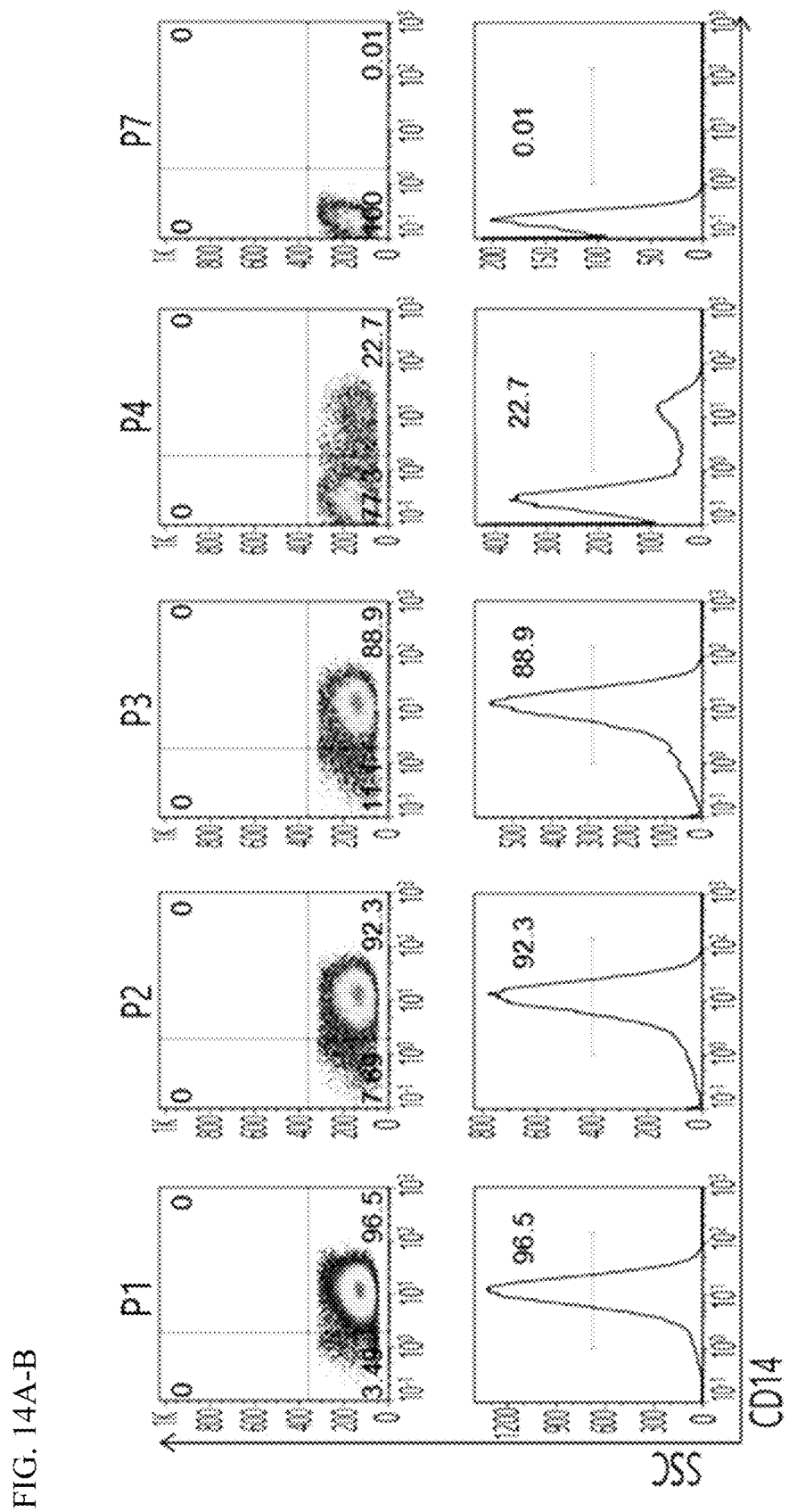
FIG. 14A-B

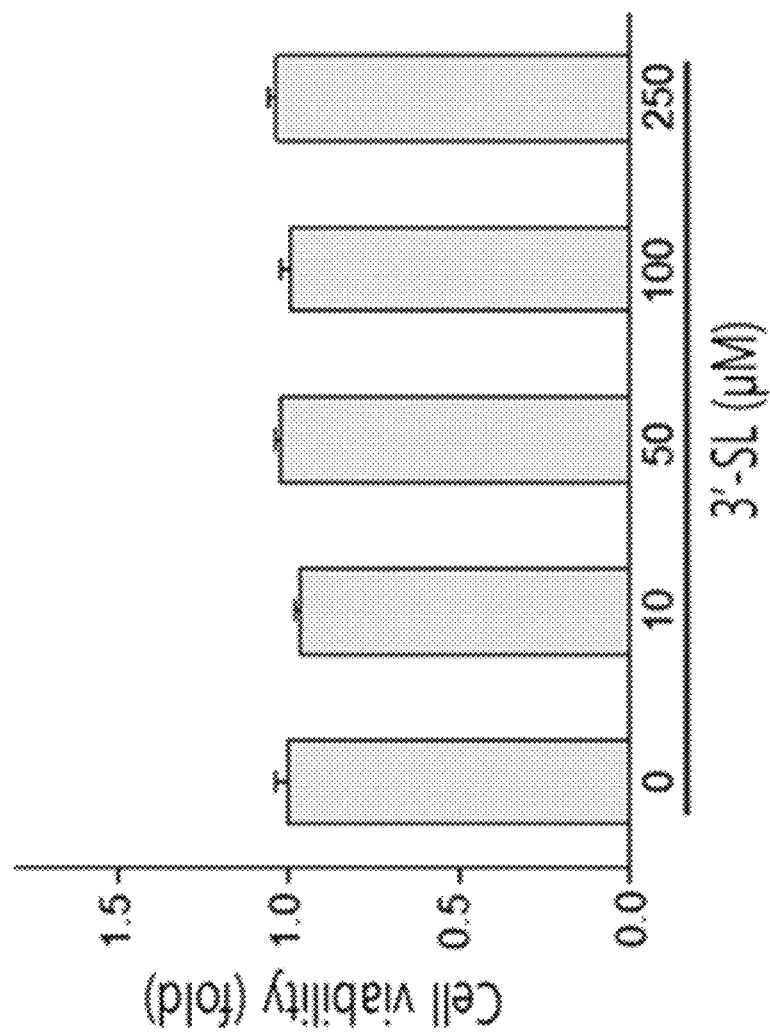
FIG. 14A-C

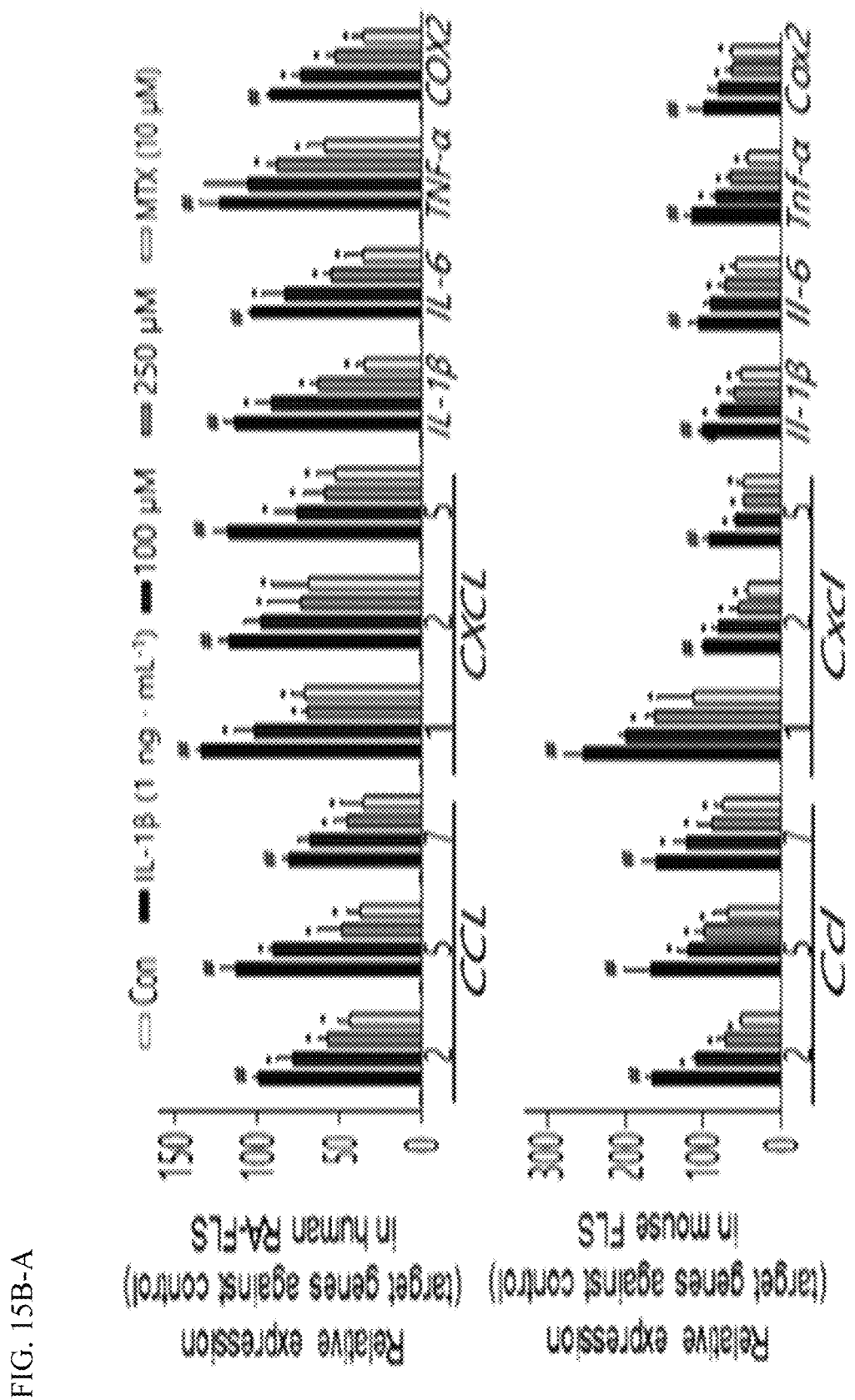
FIG. 15B-A

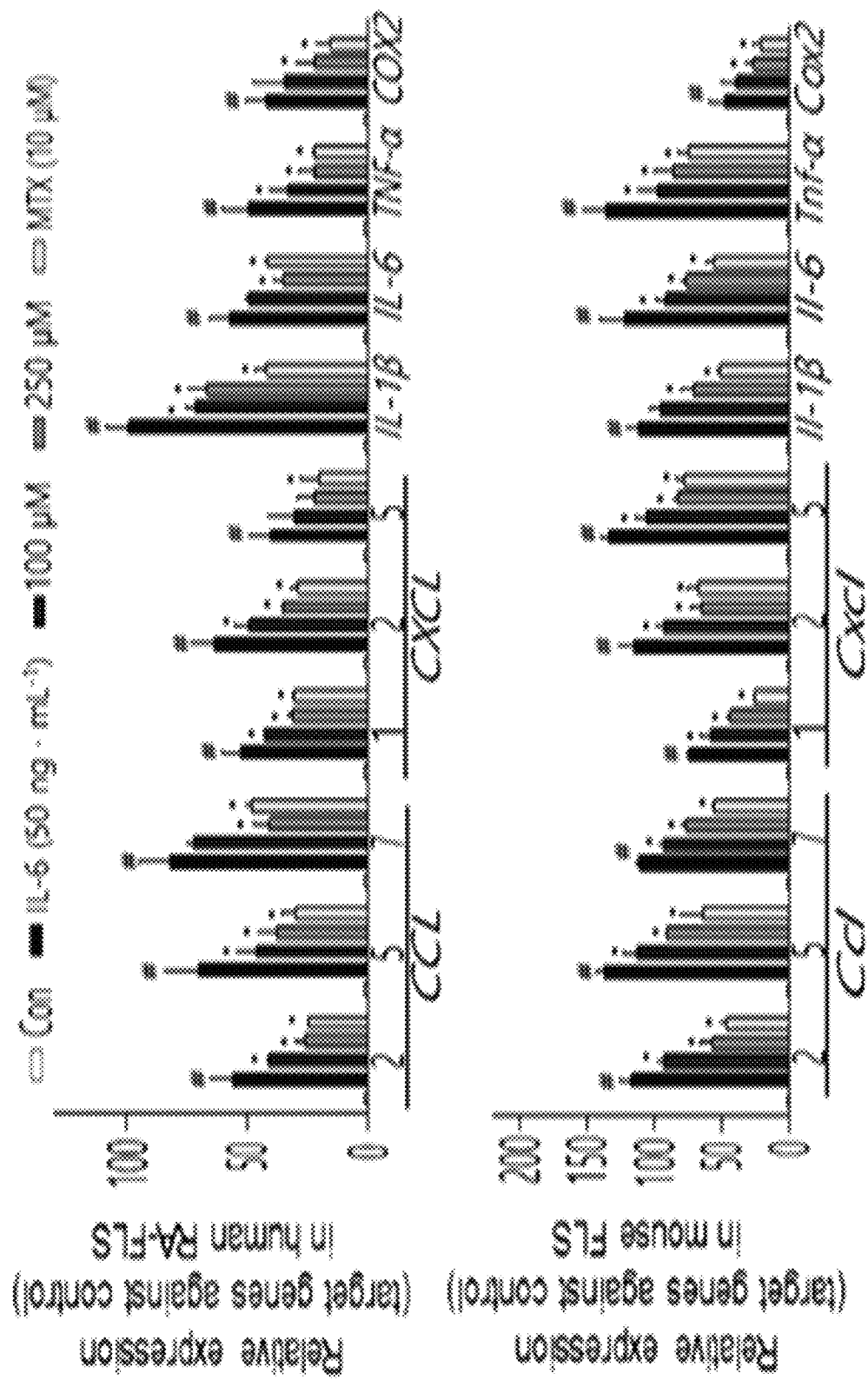
FIG. 15B-B

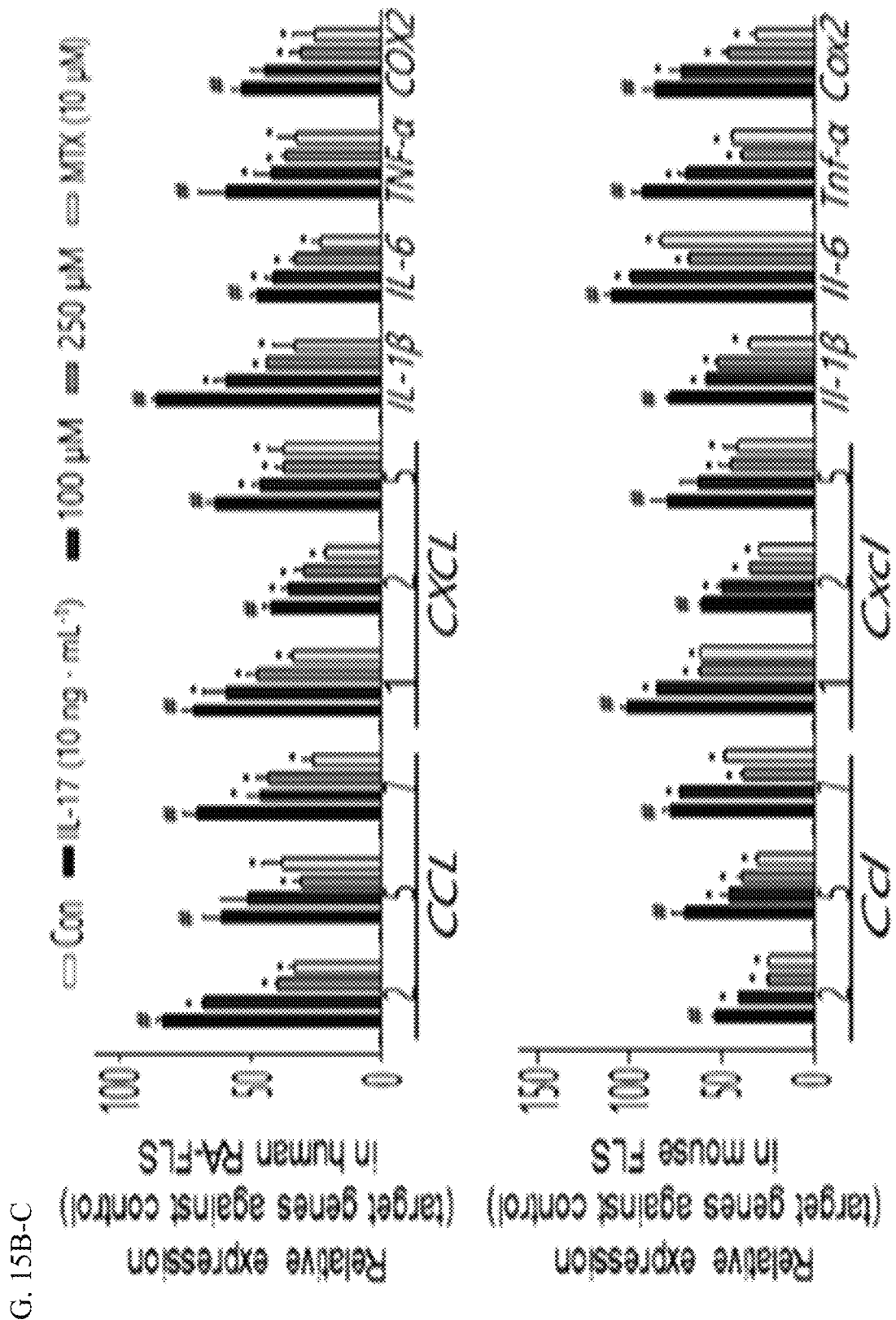
FIG. 15B-C

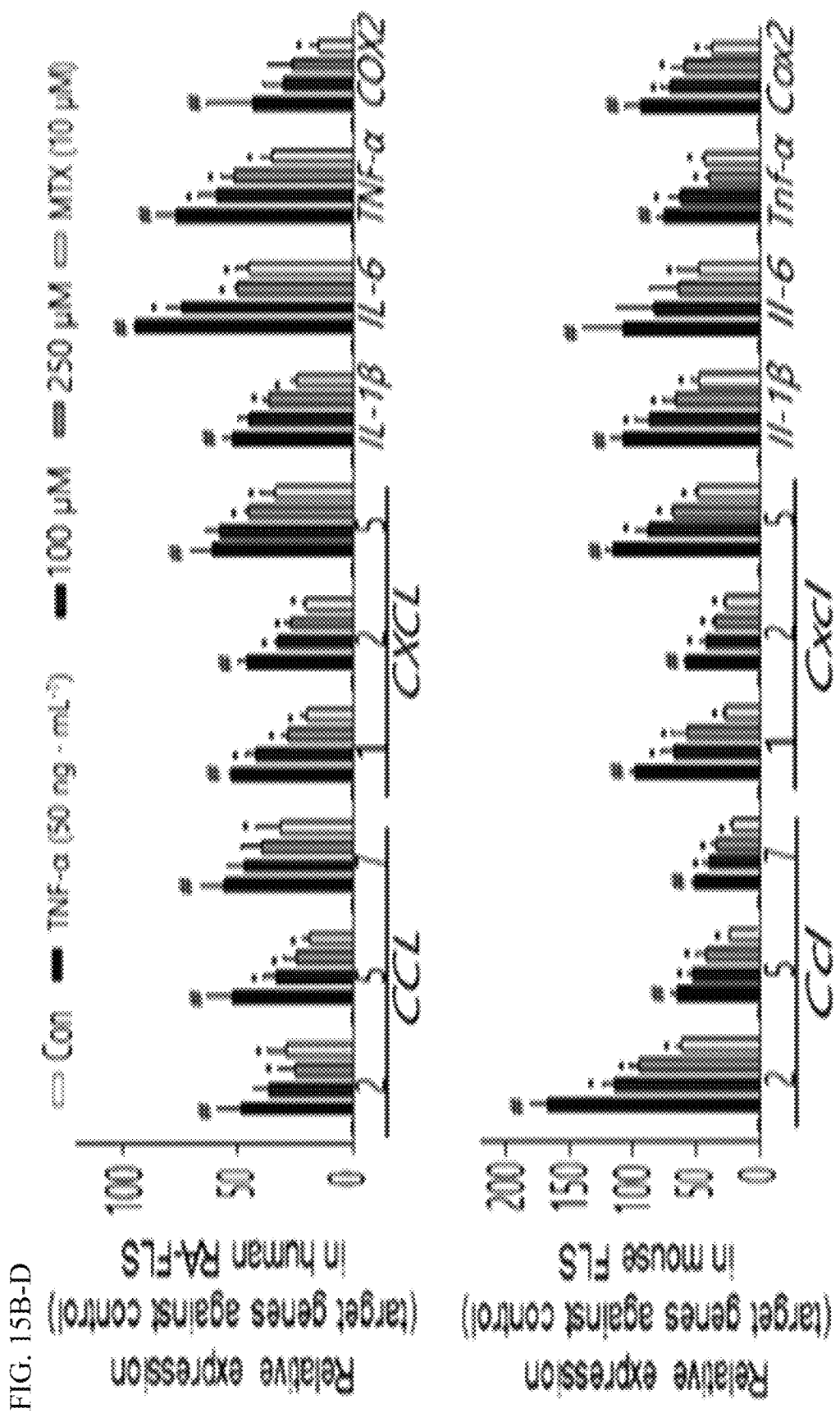
FIG. 15B-D

SEQUENCE LISTING

```
<160> NUMBER OF SEQ ID NOS: 8

<210> SEQ ID NO 1
<211> LENGTH: 22
<212> TYPE: DNA
<213> ORGANISM: Artificial Sequence
<220> FEATURE:
<223> OTHER INFORMATION: Synthetic primer

<400> SEQUENCE: 1
cacactggta agtggggcaa ga                                              22

<210> SEQ ID NO 2
<211> LENGTH: 23
<212> TYPE: DNA
<213> ORGANISM: Artificial Sequence
<220> FEATURE:
<223> OTHER INFORMATION: Synthetic primer

<400> SEQUENCE: 2
ggattgtgtt gtttcagggt tcg                                             23

<210> SEQ ID NO 3
<211> LENGTH: 19
<212> TYPE: DNA
<213> ORGANISM: Artificial Sequence
<220> FEATURE:
<223> OTHER INFORMATION: Synthetic primer

<400> SEQUENCE: 3
tcactgccac ccagaagac                                                  19

<210> SEQ ID NO 4
<211> LENGTH: 19
<212> TYPE: DNA
<213> ORGANISM: Artificial Sequence
<220> FEATURE:
<223> OTHER INFORMATION: Synthetic primer

<400> SEQUENCE: 4
tgtaggccat gaggtccac                                                  19

<210> SEQ ID NO 5
<211> LENGTH: 21
<212> TYPE: DNA
<213> ORGANISM: Artificial Sequence
<220> FEATURE:
<223> OTHER INFORMATION: Synthetic primer
```

```
<400> SEQUENCE: 5
tcctgatgtt ggtggcttca g                                              21

<210> SEQ ID NO 6
<211> LENGTH: 21
<212> TYPE: DNA
<213> ORGANISM: Artificial Sequence
<220> FEATURE:
<223> OTHER INFORMATION: Synthetic primer

<400> SEQUENCE: 6
tgtcttggca aatccggtgt a                                              21

<210> SEQ ID NO 7
<211> LENGTH: 23
<212> TYPE: DNA
<213> ORGANISM: Artificial Sequence
<220> FEATURE:
<223> OTHER INFORMATION: Synthetic primer

<400> SEQUENCE: 7
tgatggacct tctggtcttc tgg                                            23

<210> SEQ ID NO 8
<211> LENGTH: 23
<212> TYPE: DNA
<213> ORGANISM: Artificial Sequence
<220> FEATURE:
<223> OTHER INFORMATION: Synthetic primer

<400> SEQUENCE: 8
catccacatg gttgggaagt tct                                            23
```

COMPOSITION FOR INHIBITING IMMUNE CELL PROLIFERATION COMPRISING SIALYLLACTOSE OR DERIVATIVE THEREOF AND METHOD THEREOF

CROSS REFERENCE TO RELATED APPLICATIONS

The present application is a continuation application of U.S. Ser. No. 16/686,744, filed Nov. 18, 2019, which is a divisional application of U.S. Ser. No. 16/130,522, filed on Sep. 13, 2018, which is a continuation-in-part of international patent application PCT/KR2017/010489, filed on Sep. 22, 2017, the text of which is incorporated by reference, and claims the benefit of the filing date of Korean application nos. 10-2017-0067915 filed on May 31, 2017, and 10-2017-0010540 filed on Jan. 23, 2017, the texts of which are also incorporated by reference.

TECHNICAL FIELD

The present disclosure relates to a composition for inhibiting immune cell proliferation including sialyllactose or a derivative thereof as an active ingredient, and a method of inhibiting immune cell proliferation.

BACKGROUND ART

Osteoarthritis (OA) is a degenerative joint disease primarily caused by inhibition of cartilage extracellular matrix (ECM) synthesis and promotion of cartilage tissue destruction. Many etiological risk factors and pathophysiological processes associated with aging contribute to the progression of osteoarthritis. Joint instability, mechanical stress including injury, and aging-related factors that predispose one to osteoarthritis are potential osteoarthritis-causing mechanisms. These factors activate biochemical pathways in chondrocytes which are a unique cell type that synthesizes various catabolic and anabolic factors, leading to degradation of the ECM by matrix metalloproteinase (Mmp) and cessation of ECM synthesis via dedifferentiation and apoptosis of chondrocytes (Pelletier J P et al., Arthritis Rheum., 44:1237-47, 2001). In particular, cartilage tissue that constitutes a joint is not normally regenerated in vivo once it is damaged. If cartilage tissue in a joint is damaged, the cartilage tissue damage impedes daily activities with severe pain. If the damage becomes chronic, it causes fatal osteoarthritis which interferes with normal life or professional activities.

Until now, therapeutic agents for arthritis have not been developed. Generally, non-steroidal anti-inflammatory drugs (NSAIDs) are used for the purpose of alleviating joint inflammation. However, since NSAID-based drugs are primarily intended to temporarily relieve joint inflammation, NSAID-based drugs do not provide adequate treatment for osteoarthritis which is a non-inflammatory arthritis that requires enhancement of cartilage formation and inhibition of cartilage destruction (Pritchard M H et al., Annals of the Rheumatic Diseases, 37:493-503, 1978). Such NSAIDs are suitable as a therapeutic agent for the prevention of inflammation in rheumatoid arthritis which is an inflammatory arthritis. However, it is pointed out that NSAIDs accelerate cartilage damage or have adverse effects on the cardiovascular system, gastrointestinal tract, kidney, liver, etc.

Further, an autologous osteochondral transplantation method which was developed for cartilage formation involves collecting cartilage and subchondral bone from a normal part of a patient, and transplanting them into a hole which is made in the damaged cartilage site by drilling, thereby generating hyaline cartilage. Although this method has been successful in some patients, it cannot be universally applied because the method can be performed only for autologous transplant-eligible patients with less cartilage damage (Peterson L et al., J Bone Joint Surg Am. 85-A Suppl:17-24, 2003).

Meanwhile, among breast milk oligosaccharides, 3'- or 6'-sialyllactose has anti-inflammatory properties that influence intestinal microflora activity, and there is a report that 3'- or 6'-sialyllactose enriches intestinal microflora (Izquierdo-Useros N et al., Plos Biol, 2012, 10). Since sialyllactose is present in breast milk, side effects of ingesting sialyllactose have already been verified, and thus various functions thereof are being studied. Administration of sialyllactose to a patient with rheumatoid arthritis was confirmed to have therapeutic effects on autoimmune diseases caused by change in IgG (U.S. Pat. No. 5,164,374). However, there have been no reports about prophylactic and therapeutic effects of 3'- or 6'-sialyllactose on osteoarthritis.

Accordingly, the present inventors have made intensive efforts to find a novel substance capable of efficiently preventing or treating osteoarthritis, and as a result, have found that 3'- or 6'-sialyllactose may promote cartilage formation and inhibit cartilage destruction simultaneously, thereby completing the present disclosure.

DESCRIPTION OF EMBODIMENTS

Technical Problem

An object of the present disclosure is to provide a pharmaceutical composition and a food for preventing, improving, or treating osteoarthritis, the pharmaceutical composition and the food including 3'- or 6'-sialyllactose or a pharmaceutically acceptable salt thereof as an active ingredient.

Another object of the present disclosure is to provide a method of treating osteoarthritis, the method including administering the composition including 3'- or 6'-sialyllactose or a pharmaceutically acceptable salt thereof as an active ingredient.

Still another object of the present disclosure is to provide use of the composition including 3'- or 6'-sialyllactose or a pharmaceutically acceptable salt thereof as an active ingredient in the treatment of osteoarthritis.

Solution to Problem

In order to achieve the above objects, the present disclosure provides a pharmaceutical composition for preventing or treating osteoarthritis, the pharmaceutical composition including 3'- or 6'-sialyllactose or a pharmaceutically acceptable salt thereof as an active ingredient.

Further, the present disclosure provides a food for preventing or improving osteoarthritis, the food including 3'- or 6'-sialyllactose or a salt thereof acceptable for use as an active ingredient in food.

Further, the present disclosure provides a method of treating osteoarthritis, the method including administering the composition including 3'- or 6'-sialyllactose or a pharmaceutically acceptable salt thereof as an active ingredient.

Further, the present disclosure provides use of the composition including 3'- or 6'-sialyllactose or a pharmaceutically acceptable salt thereof as an active ingredient in the treatment of osteoarthritis.

Advantageous Effects of Disclosure

Sialyllactose of the present disclosure promotes cartilage formation and effectively inhibits cartilage destruction simultaneously, and therefore, is useful in the prevention or treatment of osteoarthritis. Further, the sialyllactose may alleviate an allergic reaction or inflammation of atopic dermatitis, and therefore, is useful in the prevention or treatment of atopic dermatitis.

BRIEF DESCRIPTION OF DRAWINGS

FIGS. 4A, 4B, 4C, 4D and 4E illustrate that type II collagen (Col2a1) expression was increased by treatment of chondrocytes with 0 μM, 50 μM, 100 μM, or 250 μM of 3'-sialyllactose (FIGS. 4A and 4B), Col2a1 expression which was decreased by IL-1β was increased by treatment with 3'-sialyllactose (FIGS. 4C and 4D), and Sox-9 activity which was decreased by IL-1β was increased by treatment with 3'-sialyllactose (FIG. 4E);

FIGS. 6A, 6B, 6C and 6D illustrate that Mmp3 and Mmp13 expression inducing cartilage destruction was increased by IL-1β in chondrocytes (FIGS. 6A and 6B), and Mmp3 and Mmp13 expression which was increased by IL-1β was decreased by 3'-sialyllactose (FIGS. 6C and 6D);

FIG. 10A shows a photograph of a hind paw of each treatment group at 4 weeks after arthritis induction, and FIG. 10B shows graphs illustrating hind paw swelling (A), clinical score (B), and incidence (C) of mice administered with PBS, lactose, sialic acid or 3'-sialyllactose, FIG. 10C is a graph showing production of pro-inflammatory cytokines in mouse sera at 48 days after administration of 3'-sialyllactose, and FIG. 10D shows percentages of $CD19^+B220^+$ B cells in spleens of mice administered with lactose or 3'-sialyllactose;

FIG. 11A shows a photograph of a hind paw of each treatment group at 4 weeks after arthritis induction, FIG. 11B shows graphs illustrating hind paw swelling (A), clinical score (B), and incidence (C) of mice administered with lactose, sialic acid, MTX, or 3'-sialyllactose, FIG. 11C shows graphs illustrating production of pro-inflammatory cytokines in mouse sera at 48 days after administration of 3'-sialyllactose, and FIG. 11D illustrates percentages of $CD19^+B220^+$ B cells in spleens of mice administered with lactose or 3'-sialyllactose;

FIG. 13A shows photographs of (A) fibroblast-like synoviocytes (FLS), (B) macrophages, and (C) neutrophils proliferated in the synovial tissues of ankle and knee joints of a mouse, which were stained with anti-CD90.2, anti-CD68, and elastase.

FIGS. 14A-A and 14A-B show FACS results of analyzing marker expression on the FLS surfaces in a mouse according to passages (FIG. 14A-A: CD90.2; FIG. 14A-B: CD14), and FIG. 14A-C shows a graph of cytotoxicity confirmed by WST-1 assay, and FIG. 14B is a graph showing Mmp3, Mmp13, and COX2 expression levels according to lactose, sialic acid, and 3'-sialyllactose in IL-1p-treated mouse FLS;

FIGS. 15B-A to 15B-D show whether 3'-sialyllactose inhibited chemokines and pro-inflammatory cytokines which were increased by IL-1β, IL-6, IL-17, or TNF-α in human RA-FLS and mouse FLS; FIG. 15B-A is a graph showing that 3'-sialyllactose inhibited expression of chemokines and pro-inflammatory cytokines after treatment of human RA-FLS and mouse FLS with 1 ng/mL of IL-1β, FIG. 15B-B shows that 3'-sialyllactose inhibited expression of chemokines and pro-inflammatory cytokines after treatment of human RA-FLS and mouse FLS with 50 ng/mL of IL-6, FIG. 15B-C is a graph showing that 3'-sialyllactose inhibited expression of chemokines and pro-inflammatory cytokines after treatment of human RA-FLS and mouse FLS with 10 ng/mL of IL-17, and FIG. 15B-D is a graph showing that 3'-sialyllactose inhibited expression of chemokines and pro-inflammatory cytokines after treatment of human RA-FLS and mouse FLS with 50 ng/mL of TNF-α.

BEST MODE

Figure 1:
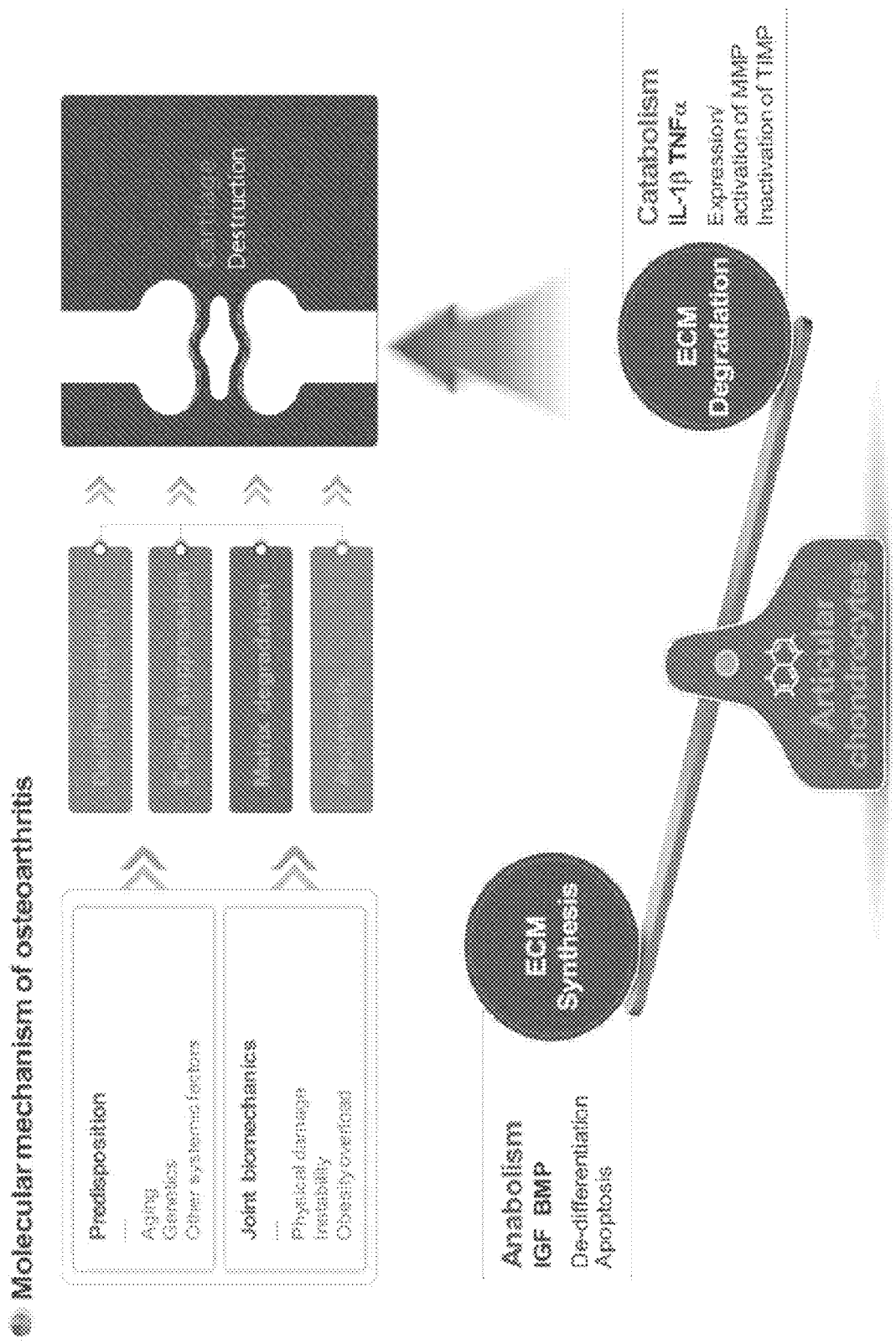
FIG. 1 illustrates a mechanism by which osteoarthritis is induced by various catabolic and anabolic factors.

Unless defined otherwise, all technical and scientific terms used herein have the same meanings as those generally understood by one of ordinary skill in the art to which the present disclosure belongs. Generally, the nomenclature used herein is well known and commonly employed in the art.

Arthritis is largely classified into non-inflammatory arthritis and inflammatory arthritis, and non-inflammatory arthritis may be represented by osteoarthritis (OA) and inflammatory arthritis may be represented by rheumatoid arthritis (Yusuf E et al., Ann Rheum Dis, 70:60-67, 2011; Berebaum F et al., Osteoarthritis Cartilage, 21:16-21, 2013).

Osteoarthritis is also called degenerative arthritis, and the etiology thereof is still obscure, but it is known that a variety of triggers such as heredity, trauma, obesity, aging, metabolic abnormalities, etc. are involved. These triggers lead to imbalance between attacking factors and defensive factors in chondrocytes, which promotes cartilage tissue destruction and cartilage wear, and as a result, patients feel pain and experience limitation in movement of the joint due to characteristic pathological changes of osteoarthritis (Pelletier J P et al., Arthritis Rheum., 44:1237-47, 2001).

In contrast, rheumatoid arthritis (RA) is known to be mainly caused by disease progression due to autoimmune reaction, unlike osteoarthritis caused by destruction of chondrocyte and cartilage tissue. Rheumatoid arthritis is an autoimmune diseases characterized by inflammation and proliferation of synoviocytes, and develops periarticular osteoporosis and bony erosion, unlike osteoarthritis. Rheumatoid arthritis is progressed by spreading of inflammation of synovial membrane to joint capsule, ligament, tendon, and invading to bone. Therefore, osteoarthritis and rheumatoid arthritis are completely different from each other in the etiology and progression, and treatment methods thereof are also different.

Therapeutic agents for rheumatoid arthritis known until now include non-steroidal anti-inflammatory drugs (NSAIDs), penicillamine, steroidal hormones, TNF inhibitors, interleukin inhibitors, JAK inhibitors, anti-CD related inhibitors, etc., which are suitable for blocking inflammation mechanism (Pritchard M H et al., Ann Rheum Dis, 37:493-503, 1978; 2014 Frost & Sullivan report: Product and pipeline analysis of the global rheumatoid arthritis therapeutics market). NSAIDs and steroidal hormone are used for osteoarthritis patients for the purpose of pain relief and anti-inflammation, but these drugs may not function as practical therapeutic agents for osteoarthritis because they aim at relieving symptoms rather than treating the disease itself (Abramson S B et al., Osteoarthritis Cartilage, 7:380-1, 1999). In addition, since osteoarthritis which is mainly caused by destruction of chondrocyte and cartilage tissue is quite different from rheumatoid arthritis which is inflammatory arthritis, in terms of the cause and symptoms, a method of treating osteoarthritis is also different from that of rheumatoid arthritis.

For example, until 2014, development of most therapeutic agents for osteoarthritis proceeded in a direction that cartilage regeneration is promoted by transplantation of various scaffolds with Col2a1 and ECM secretion-promoted mesenchymal stem cells into cartilage defects. In contrast, development of therapeutic agents for rheumatoid arthritis proceeds in a direction that inflammatory cytokines are ultimately inhibited by developing TNF inhibitors, interleukin inhibitors, JAK inhibitors, anti-CD-related inhibitors, etc. (2014 Frost & Sullivan report: 1. A product and pipeline Analysis of the Global knee cartilage repair market, 2. Product and pipeline analysis of the global rheumatoid arthritis therapeutics market). That is, it can be seen that therapeutic targets of osteoarthritis having a non-inflammatory feature and rheumatoid arthritis having an inflammatory feature take different forms according to various types of arthritis.

Based on these results, it can be seen that osteoarthritis and rheumatoid arthritis have completely different causes of disease, and therapeutic agents which are currently under development are focused on cartilage regeneration for osteoarthritis and inflammation inhibition for rheumatoid arthritis. Accordingly, target strategy for the treatment of osteoarthritis should be different from target strategy for the treatment of inflammatory rheumatoid arthritis.

As used herein, the terms "osteoarthritis (OA)" and "degenerative arthritis" may be used interchangeably with each other, and it should be understood that they have the same meanings.

In the present disclosure, it was confirmed that 3'- or 6'-sialyllactose promotes expression of type II collagen (Col2a1) that plays an important role in joint formation and inhibits expression of Mmp3 and Mmp13 that promote destruction of cartilage tissue at the same time, while having no cytotoxicity on chondrocytes. It was also confirmed that 3'- or 6'-sialyllactose is directly involved in the regulation of Sox9 which is a transcription factor involved in Col2a1 expression, and 3'-sialyllactose directly regulates the pErk signal transduction pathway involved in Mmp3 and Mmp13 expression.

Accordingly, an aspect of the present disclosure relates to a pharmaceutical composition for preventing or treating osteoarthritis, the pharmaceutical composition including sialyllactose or a pharmaceutically acceptable salt thereof as an active ingredient.

In the present disclosure, the sialyllactose may be 3'-sialyllactose or 6'-sialyllactose.

As used herein, the term "pharmaceutically acceptable salt" refers to a formulation of a compound that does not cause significant irritation to an organism to which the compound is administered and does not abrogate the biological activity and properties of the compound. The pharmaceutical salts may include acid addition salts which may form non-toxic acid addition salts containing pharmaceutically acceptable anions, for example, inorganic acids such as hydrochloric acid, sulfuric acid, nitric acid, phosphoric acid, hydrobromic acid, hydriodic acid, etc.; organic carbonic acids such as tartaric acid, formic acid, citric acid, acetic acid, trichloroacetic acid, trifluoroacetic acid, gluconic acid, benzoic acid, lactic acid, fumaric acid, maleic acid, salicylic acid, etc.; sulfonic acids such as methanesulfonic acid, ethanesulfonic acid, benzenesulfonic acid, p-toluenesulfonic acid, etc. For example, the pharmaceutically acceptable salt may also include metal salts or alkali earth metal salts formed by lithium, sodium, potassium, calcium, magnesium, etc.; amino acid salts such as lysine, arginine, guanidine, etc.; organic salts such as dicyclohexylamine, N-methyl-D-glucamine, tris(hydroxymethyl)methylamine, diethanolamine, choline, triethylamine, etc.

In the present disclosure, the pharmaceutically acceptable salt of 3'- or 6'-sialyllactose may be Na, but is not limited thereto.

The salt of 3'-sialyllactose may have a structure of the following Formula 1, and the salt of 6'-sialyllactose may have a structure of the following Formula 2, but are not limited thereto:

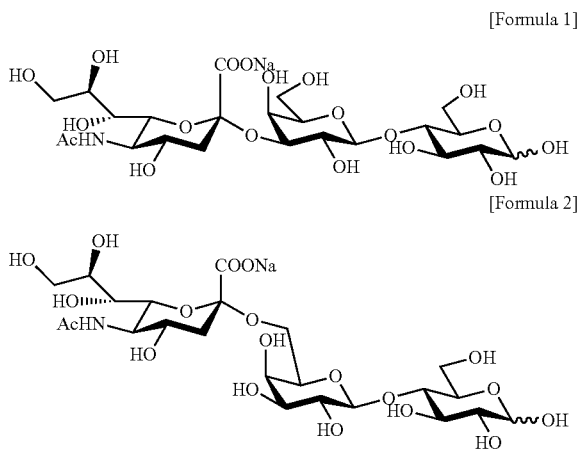

[Formula 1]

[Formula 2]

Figure 2A:
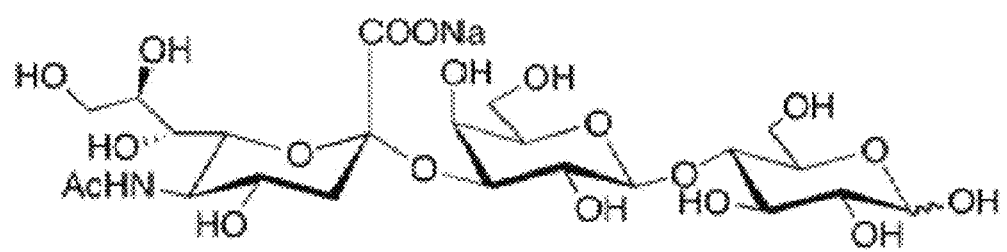
FIGS. 2A and 2B illustrate chemical structural formulae of (FIG. 2A) 3'-sialyllactose (3'-SL) and (FIG. 2B) 6'-sialyllactose (6'-SL)
Figure 2B:
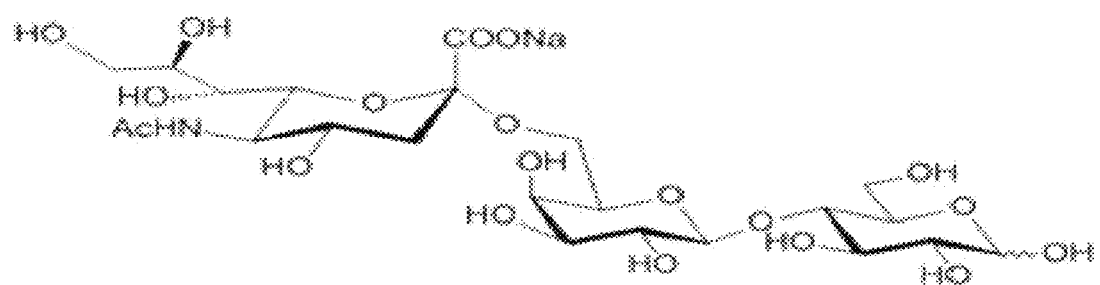

A test single compound used in the present disclosure is 3'- or 6'-sialyllactose having a structural formula of $C_{23}H_{38}NO_{19}Na$, which is a natural source-derived single compound abundant in breast milk (FIGS. 2A and 2B).

In the present disclosure, the 3'- or 6'-sialyllactose may include a derivative thereof.

As used herein, the term "derivative" refers to a compound which is modified by introduction, substitution, oxidation, reduction, etc. of functional groups of 3'- or 6'-sialyllactose without significant changes in the structure and properties of a parent compound. There is no limitation in a kind of the functional groups, and for example, the functional groups may include each independently C1 to C20 bicyclic hydrocarbon groups substituted or unsubstituted with a hydroxyl group, a phenoxy group, a thienyl group, a furyl group, a pyridyl group, a cyclohexyl group, an alkyl alcohol group, an alkyl dialcohol group, or a substituted or unsubstituted phenyl group; C3 to C30 cyclic hydrocarbon groups substituted or unsubstituted with a hydroxyl group, a hydroxymethyl group, a methyl group, or an amino group; or sugar residues, but are not limited thereto.

As used herein, the term "sugar residue" refers to a group available on elimination of one hydrogen atom from a polysaccharide molecule, and therefore, the sugar residue may be, for example, a residue derived from a monosaccharide or an oligosaccharide.

As used herein, the term "substituted" means, unless otherwise specified, that at least one hydrogen atom among functional groups is substituted with a halogen atom (F, Cl, Br, or I), a hydroxyl group, a nitro group, a cyano group, an imino group (=NH, =NR, where R is a C1 to C10 alkyl group), an amino group (—NH₂, —NH(R'), —N(R")(R'"), where R', R", R'" are each independently a C1 to C10 alkyl group), an amidino group, a hydrazine group, a hydrazone group, a carboxyl group, a C1 to C20 alkyl group, C6 to C30 aryl group, a C3 to C30 cycloalkyl group, a C3 to C30 heteroaryl group, or a C2 to C30 heterocycloalkyl group.

In the present disclosure, a pH range at which the 3'- or 6'-sialyllactose or 3'- or 6'-sialyllactose derivative shows stability may be pH 4 to pH 10, but is not limited thereto.

In the present disclosure, the pharmaceutical composition for preventing or treating osteoarthritis including 3'- or 6'-sialyllactose as an active ingredient may have one or more of the following properties of:

1) increasing expression of type II collagen (Col2a1);
2) decreasing expression of matrix metalloproteinase3 (Mmp3) or matrix metalloproteinase13 (Mmp13);
3) increasing Sox-9 activity; and
4) increasing inactivation of p-ERK.

In the present disclosure, the pharmaceutical composition may further include a pharmaceutically acceptable carrier, excipient, or diluent. The "pharmaceutically acceptable carrier" refers to a substance that may be added to the active ingredient to aid preparation or stabilization of a formulation without causing a significant adverse toxicological effect on a patient.

The carrier refers to a carrier or diluent that does not cause irritation to a patient and does not abrogate the biological activity and properties of 3'- or 6'-sialyllactose of the present disclosure. When the composition is formulated into a liquid solution, the pharmaceutically acceptable carrier may be a mixture of one or more of saline, sterile water, Ringer's solution, buffered saline, an albumin injectable solution, a dextrose solution, a maltodextrin solution, glycerol, and ethanol, which are sterile and biocompatible. If necessary, other common additives, including an antioxidant, a buffer, a bacteriostatic agent, etc. may be added thereto. Further, a diluent, a dispersant, a surfactant, a binder, and a lubricant may be additionally added thereto to prepare the composition as a formulation for injection such as an aqueous solution, a suspension, and an emulsion, or as a pill, a capsule, a granule, or a tablet. Other carriers are described, for example, in a literature [Remington's Pharmaceutical Sciences (E. W. Martin)].

Pharmaceutically acceptable carriers may include sterile aqueous solutions or dispersions and sterile powders for extemporaneous preparation of sterile injectable solutions or dispersion. The use of such media and agents for pharmaceutically active substances is known in the art. The composition may be formulated for parenteral injection. The composition may be formulated as a solution, microemulsion, liposome, or other ordered structure suitable to high drug concentration. The carrier may be a solvent or dispersion medium containing, for example, water, ethanol, polyol (e.g., glycerol, propylene glycol, and liquid polyethylene glycol, etc.), and suitable mixtures thereof. In some cases, the composition may include isotonic agents, for example, sugars, polyalcohols such as mannitol, sorbitol, or sodium chloride. Sterile injectable solutions may be prepared by incorporating a required amount of 3'- or 6'-sialyllactose in an appropriate solvent with one or a combination of ingredients described above, as required, followed by sterilization microfiltration. Generally, dispersions are prepared by incorporating the active compound into a sterile vehicle that contains a basic dispersion medium and the required other ingredients from those described above. In the case of sterile powders for the preparation of sterile injectable solutions, preparation methods are vacuum drying and freeze-drying (lyophilization) that yield a powder of the active ingredient and any additional desired ingredient from a previously sterile-filtered solution thereof.

Further, the pharmaceutical composition according to the present disclosure may be administered orally or parenterally in an administration dose and frequency which may vary depending on severity of a patient suffering from pain. The composition may be administered to a patient in a bolus or continuous form, as needed.

A preferred administration dosage of the pharmaceutical composition for preventing or treating osteoarthritis according to the present disclosure may vary depending on a patient's condition, body weight, severity of a disease, a type of a drug, administration route and period, but may be appropriately selected by those skilled in the art. However, for preferred effects, the pharmaceutical composition may be administered at a daily dose of 0.0001 mg/kg to 2,000 mg/kg, preferably 0.001 mg/kg to 2,000 mg/kg. The composition may be administered once or several times a day. However, the scope of the present disclosure is not limited to the above administration dosage.

The pharmaceutical composition for preventing or treating osteoarthritis according to the present disclosure may be administered to rats, mice, livestock, and mammals including humans via various routes. All modes of administration are contemplated, for example, orally, rectally or by intravenous, intramuscular, subcutaneous, intrauterine, or intracerebroventricular injection.

The composition including sialyllactose of the present disclosure may inhibit cartilage destruction due to aging of the joint and may promote cartilage formation, thereby treating osteoarthritis.

Methods of treating osteoarthritis known until now may include replacement arthroplasty, arthroplasty, joint transplantation, and autologous chondrocyte implantation. However, since replacement arthroplasty requires joint incision, it impose pain and burden on a patient, and the procedure is complicated and difficult. In addition, replacement arthroplasty is performed only for autologous transplant-eligible patients, and thus there are many restrictions in the treatment (Peterson L et al., J Bone Joint Surg Am, 85:17-24, 2003). Autologous chondrocyte implantation is a method of obtaining chondrocytes from a cartilage tissue collected from a normal site of a patient, culturing and proliferating the desired number of the chondrocytes ex vivo, and then introducing the chondrocytes into a damaged site of cartilage. However, this procedure is also complicated and difficult, because donor tissues are limited, and a surgery is required for collection of a tissue for implantation (Yoon et al., Journal of Rheumatic Diseases, 19, 2012). In addition, there is a method of obtaining mesenchymal stem cells from a tissue such as autologous bone marrow, muscle, fat, etc., differentiating the cells ex vivo, and then injecting the cells into a damaged site of cartilage. However, there is a risk that mesenchymal stem cells may differentiate into hypertrophic chondrocytes when TGF-b is used to induce differentiation of mesenchymal stem cells into chondrocytes, and mesenchymal stem cells may differentiate into osteophytes when BMP is used to induce differentiation of mesenchymal stem cells into chondrocytes (1. Park et al., J of Korean Orthopaedic Research Society, 18:2, 2015; Mamidi M K et al., Osteoarthritis Cartilage, 24:1307-16, 2016). Substantially, most drugs or health foods for osteoarthritis which have been developed until now tend to focus on pain relief and anti-inflammation effects rather than focusing on chondrocyte activation and cartilage regeneration which are critical to osteoarthritis treatment.

Therefore, 3'- or 6'-sialyllactose which is one of breast milk components having no adverse effect on human body is expected to be used as a raw material that may prevent, treat, or improve osteoarthritis and may solve problems of the known therapeutic drugs or health foods for osteoarthritis, including side effects, reduced cartilage regeneration effects, and safety.

Another aspect of the present disclosure relates to a method of treating osteoarthritis, the method including administering the composition including sialyllactose or a pharmaceutically acceptable salt thereof as an active ingredient.

Still another aspect of the present disclosure relates to use of the composition including sialyllactose or a pharmaceutically acceptable salt thereof as an active ingredient in the treatment of osteoarthritis.

In the present disclosure, the sialyllactose may be 3'-sialyllactose or 6'-sialyllactose, and more preferably, the salt of 3'-sialyllactose may have a structure of the following Formula 1, and the salt of 6'-sialyllactose may have a structure of the following Formula 2, but are not limited thereto:

[Formula 1]

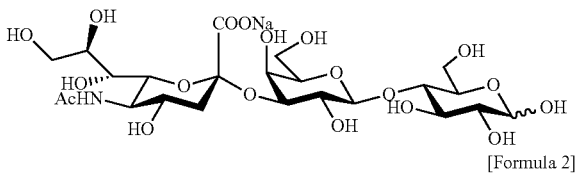

[Formula 2]

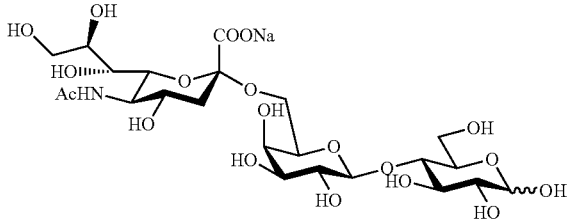

Still another aspect of the present disclosure relates to a food for preventing or improving osteoarthritis, the food including sialyllactose or a salt thereof acceptable for use as an active ingredient in food.

In the present disclosure, the sialyllactose may be 3'-sialyllactose or 6'-sialyllactose.

In the present disclosure, the salt of 3'-sialyllactose acceptable for food use may have the structure of Formula 1, and the salt of 6'-sialyllactose acceptable for food use may have the structure of Formula 2, but are not limited thereto.

In the present disclosure, the salt of 3'- or 6'-sialyllactose acceptable for food use may be Na, but is not limited thereto.

In the present disclosure, the 3'- or 6'-sialyllactose may include a derivative thereof.

The food of the present disclosure may be prepared in any form of a functional food, a nutritional supplement, a health food, and a food additive. For example, as the health food, the 3'-sialyllactose of the present disclosure may be drunken after being prepared in a form of teas, juices, and drinks, or may be taken after granulation, encapsulation, and powdering. Further, the functional food may be prepared by adding 3'-sialyllactose of the present disclosure to beverages (including alcoholic beverages), fruits and their processed foods (e.g., canned fruits, bottled foods, jam, marmalade, etc.), fish, meat, and their processed food (e.g., ham, sausage, corn beef, etc.), breads and noodles (e.g., udon noodles, buckwheat noodles, ramen noodles, spaghetti, macaroni, etc.), fruit juices, various drinks, cookies, taffy, dairy products (e.g., butter, cheese, etc.), edible vegetable oils, margarine, vegetable proteins, retort foods, frozen foods, various seasonings (e.g., soybean paste, soy sauce, sauce, etc.), etc.

Further, the health functional food includes various forms, such as functional food, nutritional supplements, health food, and food additives, as a food composition, and may be provided in various forms according to a general method known in the art, for example, by preparing the 3'- or 6'-sialyllactose in a form of tea, juice, or drink, or by granulating, encapsulating, or powdering the 3'- or 6'-sialyllactose, or adding the compound or the extract to various foods including beverages, fruits and their processed foods, fish, meat and their processed foods, breads, noodles, seasonings, etc.

The present disclosure provides a method of promoting cartilage formation, the method including administering a therapeutically effective amount of sialyllactose or a pharmaceutically acceptable salt thereof to a patient in need of treatment. A detailed description of the sialyllactose is the same as described above.

Specifically, the sialyllactose may promote cartilage formation by increasing expression of type II collagen (Col2a1) which is suppressed by IL-1β in chondrocytes.

The present disclosure provides a method of inhibiting cartilage destruction, the method including administering a therapeutically effective amount of sialyllactose or a pharmaceutically acceptable salt thereof to a patient in need of treatment. A detailed description of the sialyllactose is the same as described above.

The sialyllactose may decrease expression of Mmp3 and Mmp13 which are increased by IL-1β in chondrocytes. Specifically, the sialyllactose may alleviate and inhibit cartilage destruction by inhibiting the Erk signal transduction pathway which is able to activate Mmp3 and Mmp13 increased by IL-1β.

The present disclosure provides a method of preventing or treating atopic dermatitis, the method including administering a therapeutically effective amount of sialyllactose or a pharmaceutically acceptable salt thereof to a patient in need of treatment. A detailed description of the sialyllactose is the same as described above.

In an embodiment, it was confirmed that an atopic dermatitis mouse model which was orally administered with sialyllactose showed reduction in the ear thickness, specifically, reduction in the epidermal and dermal thickness. It was also confirmed that the number of mast cells in the ear skin of the mouse was decreased in a concentration-dependent manner. Accordingly, the sialyllactose may alleviate an allergic reaction or inflammation of atopic dermatitis, thereby decreasing the skin thickness.

Mode of Disclosure

Hereinafter, the present disclosure will be described in more detail with reference to embodiments. However, it is apparent to those skilled in the art that these embodiments are for more detailed explanation, and the scope of the present disclosure is not intended to be limited by these embodiments.

Example 1: Measurement of Cytotoxicity of Sialyllactose on Chondrocytes

Chondrocytes were obtained from cartilage tissues derived from femoral heads, femoral condyles, and tibial plateaus of normal mouse at 5 days after birth. The obtained chondrocytes were cultured in DMEM medium (Gibco, USA) containing 10% (v/v) fetal bovine serum (Gibco, USA), 50 μg/ml of streptomycin (Sigma-Aldrich, USA) and 50 unit/ml of penicillin (Sigma-Aldrich, USA).

In order to confirm that 3'- or 6'-sialyllactose has no cytotoxicity on chondrocytes, chondrocytes were cultured in a 96-well culture plate at a density of $9 \times 10^3$ cells/well, and then treated with 3'- or 6'-sialyllactose (Genechem Inc., Daejeon, Korea) at a concentration of 0 μM, 10 μM, 50 μM, 100 μM, or 250 μM, followed by incubation in a 5% $CO_2$ incubator at 37° C. for 24 hrs. Cytotoxicity of 3'- or 6'-sialyllactose on chondrocytes was confirmed by measuring absorbance at 450 nm using an EZ-Cytox Cell viability assay kit (DoGen, Korea).

Figure 3A:
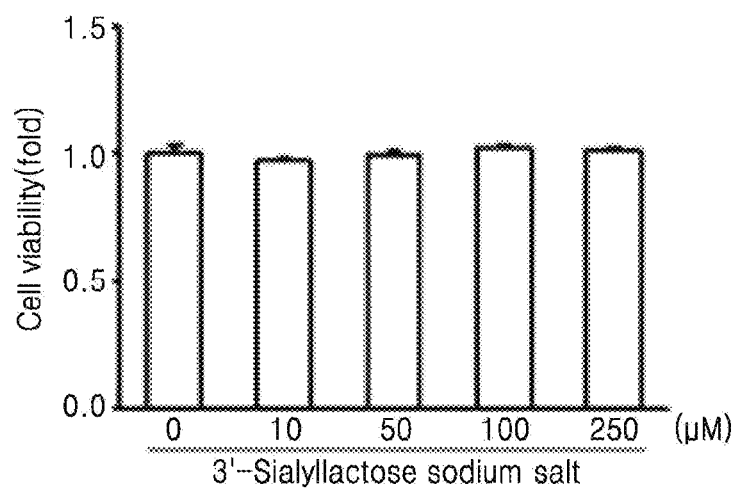
FIGS. 3A and 3B illustrate that 3'-sialyllactose and 6'-sialyllactose did not show cytotoxicity against chondrocytes when chondrocytes were treated with (FIG. 3A) 3'-sialyllactose or (FIG. 3B) 6'-sialyllactose at various concentrations.
Figure 3B:
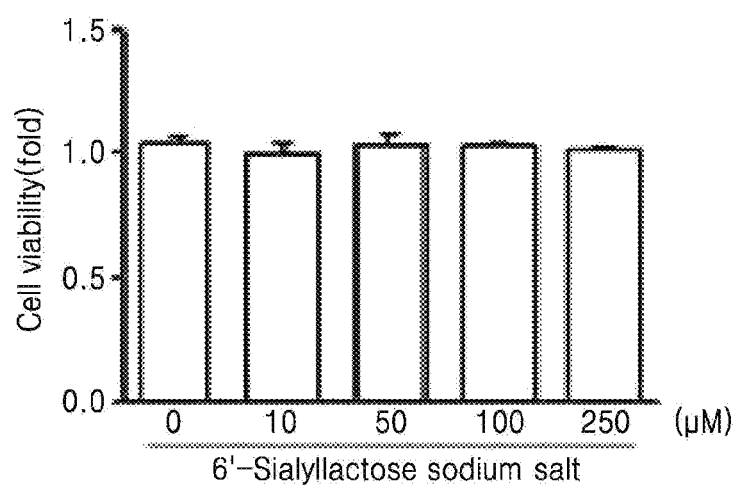

As a result, 3'-sialyllactose and 6'-sialyllactose did not show cytotoxicity on chondrocytes at any concentration, suggesting that they do not adversely affect chondrocyte proliferation (FIGS. 3A and 3B).

Example 2: Examination of Effects of Sialyllactose on Cartilage Formation and Regeneration 2-1: Increase of Expression of Type II Collagen (Col2a1)

In order to examine effects of 3'- or 6'-sialyllactose on cartilage formation and regeneration, the chondrocytes obtained in Example 1 were incubated for 36 hrs and then treated with 3'- or 6'-sialyllactose at a concentration of 0 μM, 10 μM, 50 μM, 100 μM, or 250 μM, followed by further incubation for 36 hrs.

Next, in order to perform qRT-PCR, RNA was extracted from the chondrocytes using a TRI reagent (Molecular Research Center Inc.), and cDNA obtained by reverse transcription of RNA was amplified by PCR using primers of SEQ ID NOS: 1 and 2 under condition of annealing temperature of 55° C. to examine expression of type II collagen (Col2a1, 173 bp) which is essential for cartilage formation. As a control group, Gapdh (450 bp, annealing temperature of 58° C.) was examined by using primers of SEQ ID NOS: 3 and 4.

```
SEQ ID NO: 1:
5'-CACACTGGTAAGTGGGGCAAGA-3'  (Col2a1-S)

SEQ ID NO: 2:
5'-GGATTGTGTTGTTTCAGGGTTCG-3'  (Col2a1-AS)

SEQ ID NO: 3:
5'-TCACTGCCACCCAGAAGAC-3'  (Gapdh-S)

SEQ ID NO: 4.
5'-TGTAGGCCATGAGGTCCAC-3'  (Gapdh-AS)
```

Further, a whole cell lysate was extracted from the chondrocytes using a lysis buffer (150 mM NaCl, 1% NP-40, 50 mM Tris, 5 mM NaF) containing protease and phosphatase inhibitor cocktails (Roche), and Col2a1 expression in the cells was examined. Western blotting was performed using anti-Col2a1 antibody (Millipore) and anti-Erk antibody (Cell signaling), and thickness and concentration of Western blot bands were measured by a computer program and relative values thereof were determined by densitometry (FIGS. 4A and 4B).

Figure 5A:
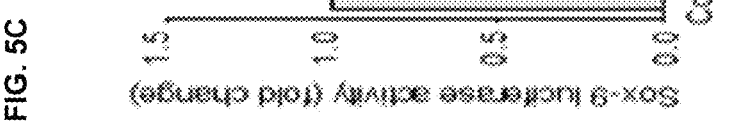
FIGS. 5A, 5B and 5C illustrate that type II collagen (Col2a1) expression was increased by treatment of chondrocytes with 0 μM, 50 μM, 100 μM, or 250 μM of 6'-sialyllactose (FIG. 5A), Col2a1 expression which was decreased by IL-1β was increased by treatment with 6'-sialyllactose (FIG. 5B), and Sox-9 which is a transcription factor that regulates type II collagen expression was decreased by IL-1β but increased again by 6'-sialyllactose (FIG. 5C)

As a result, it was confirmed that Col2a1 expression in chondrocytes was increased by 3'-sialyllactose or 6'-sialyllactose, indicating that 3'-sialyllactose and 6'-sialyllactose have the effect of promoting cartilage formation (FIGS. 4A and 4B and FIG. 5A).

2-2: Increase of Expression of Type II Collagen (Col2a1) Suppressed by IL-1β

IL-1β is a representative inflammatory cytokine inhibiting Col2a1 expression in chondrocytes. Chondrocytes were incubated for 36 hrs, and then treated with 5 ng/ml of IL-1β (GeneScript, USA) for 24 hrs to confirm that Col2a1 expression was decreased by IL-1β.

In order to examine whether the decreased Col2a1 expression is increased again in chondrocytes by 3'- or 6'-sialyllactose, qRT-PCR and Western blotting were performed in the same manner as in Example 2-1.

Figure 5B:
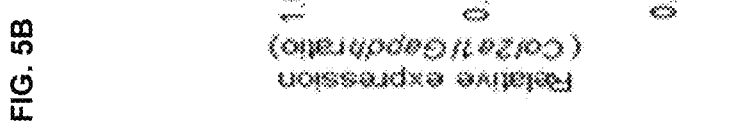

As a result, it was confirmed that Col2a1 expression suppressed by IL-1β in chondrocytes was gradually increased by 3'- or 6'-sialyllactose (FIGS. 4C and 4D and FIG. 5B), indicating that cartilage formation and regeneration may be promoted by 3'-sialyllactose or 6'-sialyllactose.

Example 3: Activation of Cartilage Formation and Regeneration Signaling Pathways by Sialyllactose Col2a1 expression essential for cartilage formation and regeneration is regulated by a transcription factor Sox-9, and therefore, it was examined whether Sox-9 transcription factor is regulated by 3'-sialyllactose.

A Sox-9 reporter gene was prepared by inserting 48-bp Sox9 binding site in the first intron of human Col2a1 gene into the upstream of SV40 promoter in pGL3 vector (Zhou G et al., J Biol Chem 1998, 12, 14989-97).

1 µg of the Sox-9 reporter gene was transfected into chondrocytes using lipofectamine 2000 (Invitrogen) for 3 hrs. The transfected cells were co-treated with 5 ng/ml interleukin 1 beta (IL-1β) and 0 µM, 10 µM, 50 µM, 100 µM, or 250 µM of 3'- or 6'-sialyllactose for 24 hrs, and then chondrocytes were recovered to examine Sox-9 activity by luciferase activity.

Figure 5C:
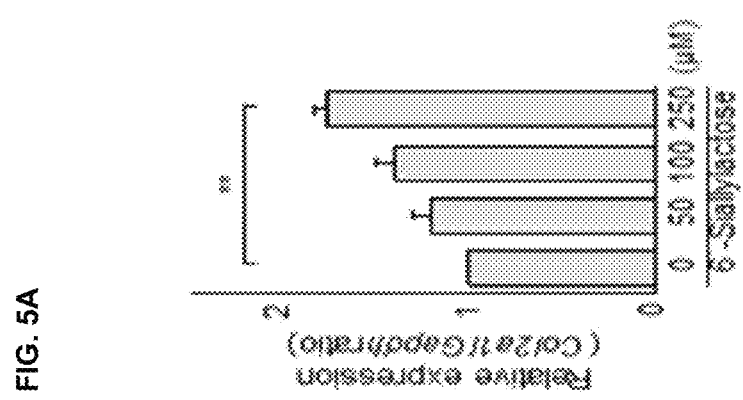

As a result, it was confirmed that Sox-9 activity decreased by IL-1β was restored by 3'- or 6'-sialyllactose (FIG. 4E and FIG. 5C), indicating that 3'- or 6'-sialyllactose directly regulates Sox-9 activity, leading to regulation of Col2a1 expression essential for cartilage formation. In other words, cartilage formation and regeneration are promoted by 3'-sialyllactose or 6'-sialyllactose.

Example 4: Examination of Inhibition of Articular Inflammation and Cartilage Destruction by Sialyllactose IL-1β is a representative inflammatory cytokine that decreases Col2a1 essential for cartilage formation in chondrocytes and also promotes articular inflammation and cartilage tissue destruction. Chondrocytes were treated with 5 ng/ml of IL-1β by time, and then qRT-PCR was performed using conditions and primers of the following Table 1 according to the method of Example 2-1 to examine inhibition of Mmp3 and Mmp13 expression.

TABLE 1

| SEQ ID NO. | Sequence (5'-3') | Sense/Antisense | Gene | Size (bp) | Annealing temperature (AT, °C.) |
|---|---|---|---|---|---|
| 5 | TCCTGATGTTGGTGGCTTCAG | S | Mmp3 | 102 | 58 |
| 6 | TGTCTTGGCAAATCCGGTGTA | AS | | | |
| 7 | TGATGGACCTTCTGGTCTTCTGG | S | Mmp13 | 473 | 55 |
| 8 | CATCCACATGGTTGGGAAGTTCT | AS | | | |

Secretory proteins such as Mmp3 and Mmp13 were allowed to react at 0° C. for 20 min after reacting 900 µl of serum-free medium (conditioned medium) with 100 µl of trichloroacetic acid (TCA). Next, a supernatant was discarded by centrifugation at 12,000 rpm and 4° C. for 10 min, and then reacted with 500 µl of 100% cold acetone at 20° C. for 1 hr. The sample reacting with 100% acetone was centrifuged to discard a supernatant, and proteins were finally precipitated and detected. Western blotting was performed using anti-Mmp3 antibody (Abcam) and anti-Mmp13 antibody (Abcam), and thickness and concentration of Western blot bands were measured by a computer program and relative values thereof were determined by densitometry.

Figure 7A:
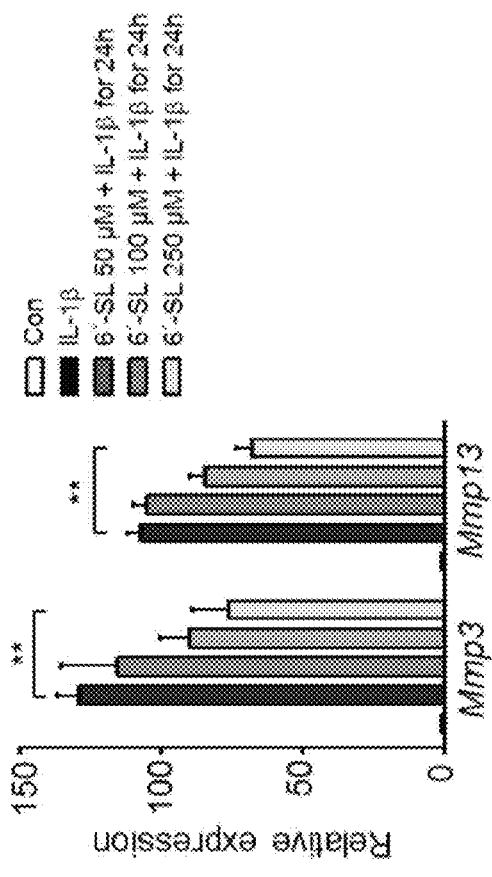
FIGS. 7A and 7B illustrate that Mmp3 and Mmp13 expression inducing cartilage destruction was increased by IL-1β in chondrocytes (FIG. 7A), and Mmp3 and Mmp13 expression which was increased by IL-1β was decreased by 6'-sialyllactose (FIG. 7B)

As a result, it was confirmed that Mmp3 and Mmp13 expression which induces cartilage tissue destruction causing articular inflammation was increased in chondrocytes by IL-1β (FIGS. 6A, 6B, and 7A).

Figure 7B:
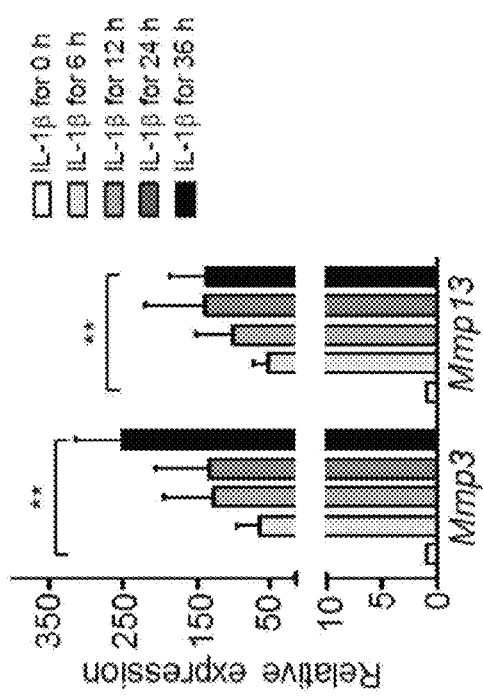

Accordingly, the chondrocytes were treated with 5 ng/ml of IL-1β and 0 µM, 10 µM, 50 µM, 100 µM, or 250 µM of 3'- or 6'-sialyllactose for 24 hrs to examine Mmp3 and Mmp13 expression levels. qRT-PCR was performed using the conditions and primers of Table 1, and Western blotting was performed to confirm that Mmp3 and Mmp13 expression increased by IL-1β in chondrocytes was decreased by 3'- or 6'-sialyllactose in a concentration-dependent manner (FIGS. 6C, 6D, and 7B), indicating that articular inflammation and cartilage tissue destruction may be alleviated and inhibited by 3'-sialyllactose or 6'-sialyllactose.

Example 5: Inhibition of Cartilage Destruction Signal Transduction Pathway by Sialyllactose Mmp3 and Mmp13 which are cartilage-destroying factors and are increased by IL-1β are activated via various signal transduction pathways in chondrocytes. Accordingly, it was examined whether 3'-sialyllactose is able to block various signal transduction pathways which are regulated by IL-1β.

Chondrocytes of mouse knee joint were treated with 5 ng/ml of IL-1β for 10 min to examine activation of extracellular-signal regulated kinase (Erk) through Erk phosphorylation.

Figure 8:
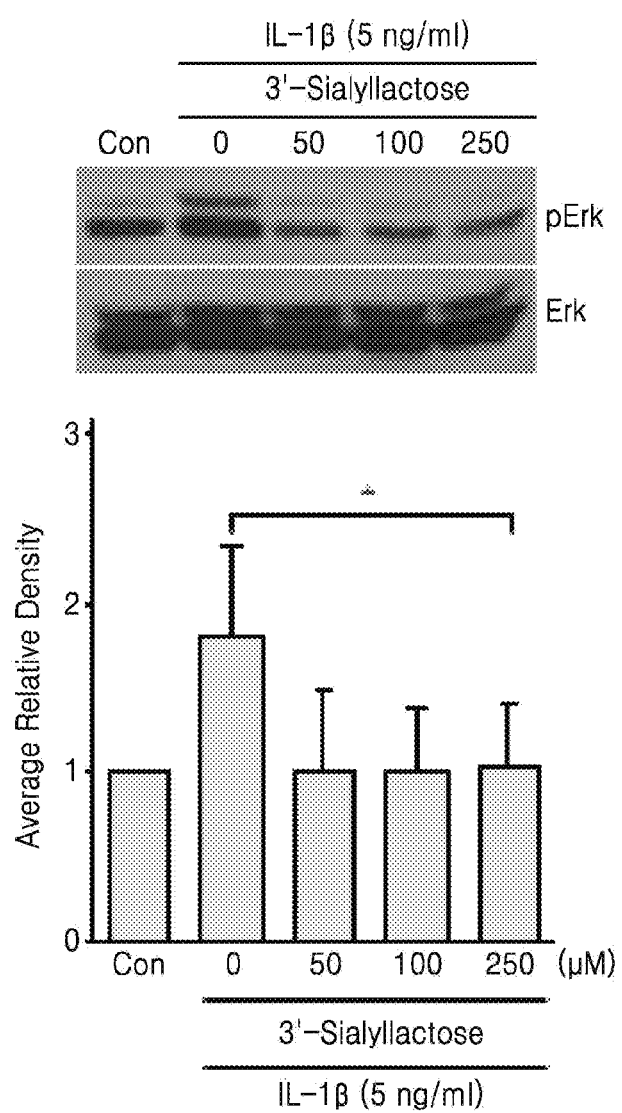
FIG. 8 illustrates that Erk phosphorylation that was increased by IL-1β in chondrocytes was inactivated by 3'-sialyllactose.

Chondrocytes were co-treated with 5 ng/ml of IL-1β and 0 μM, 50 μM, 100 μM, or 250 μM of 3'-sialyllactose, and Erk phosphorylation increased by IL-1β was confirmed to be decreased by 3'-sialyllactose (FIG. 8). That is, Western blotting and densitometry showed that among the signal transduction pathways capable of activating Mmp3 and Mmp13 by IL-18, Erk signal transduction pathway may be inhibited by 3'-sialyllactose, thereby inhibiting Mmp3 and Mmp13.

In general, Erk activation or promotion is also found in tissues of osteoarthritis patients (Yang et al., Nat Med, 2010), suggesting that 3'-sialyllactose may strongly inhibit the cartilage destruction signaling pathway that is most involved in osteoarthritis patients.

Example 6. Examination of In Vivo Articular Inflammation Inhibition by 3'-Sialyllactose 6-1. Osteoarthritis Mouse Model Induced by Destabilization of Medial Meniscus and Oral Administration In order to evaluate the role of 3'-sialyllactose in vivo, it was examined whether 3'-sialyllactose administration may inhibit osteoarthritis development in DMM-induced osteoarthritis models.

All animal experiments were approved by the Animal Care and Use Committee of the University of Ajou. For osteoarthritis models, 8-week-old male C57BL/6 mice were subjected to destabilization of the medial meniscus (DMM) surgery. Mice knee joints were processed for histological analysis 10 weeks after surgery. In detail, the experimental mice also received gavage feeding of PBS containing 3'-sialyllactose (100 mg/Kg) starting at 2 weeks prior to DMM, and oral feeding on every other day during 4 weeks after surgery, and performed three times a week for total 6 weeks until the end of the experiment. Then, the mice were sacrificed. Control mice were administered with PBS in the same manner.

6-2. Evaluation of Cartilage Destruction and Immunohistochemistry

Knee joints of the mice sacrificed in Example 6-1 were fixed in 4% paraformaldehyde, treated with 0.5 M EDTA (pH 8.0) for 2 weeks, and embedded in paraffin. The paraffin blocks were sectioned at a thickness of 5 μm and serial-sectioned at 40-μm intervals. The paraffin sections were deparaffinized in xylene and hydrated with graded ethanol. Cartilage destruction was detected by Safranin-O staining and scored using the Osteoarthritis Research Society International (OARSI) grading system. Mmp3 (ab52915), Mmp13 (ab51072), Cox2 (SC-1745), pErk ((#9101), IjB (9242), Sox9 (NBP2-24659; Novus, Littleton, USA) and Col2a1 (MAB8887) were immunostained as previously described.

Figure 9A:
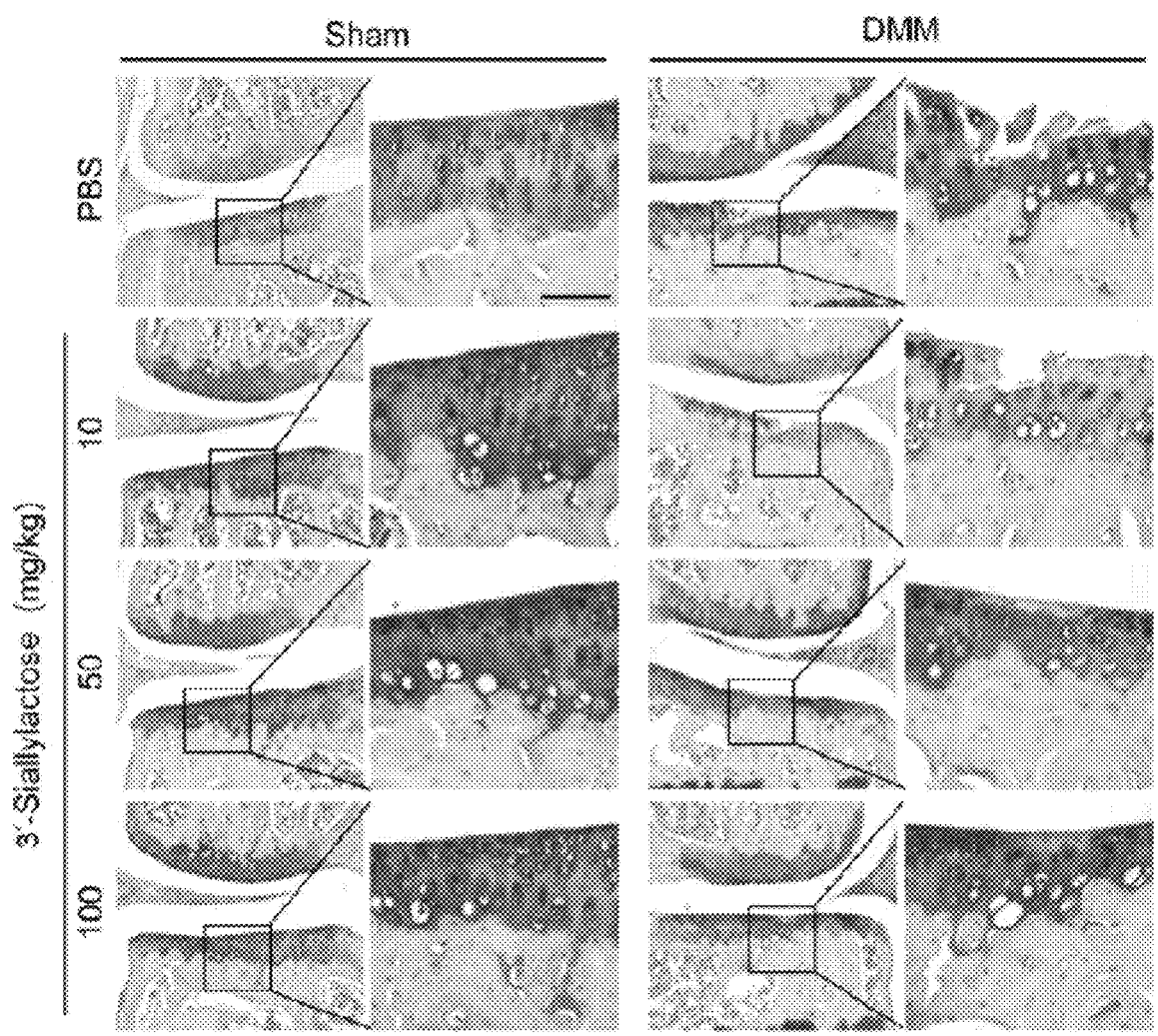
FIG. 9A shows photographs of Safranin-O staining of cartilage destruction in a DMM-induced osteoarthritis mouse model that had received gavage feeding of 3'-sialyllactose three times a week and a control mouse.
Figure 9B:
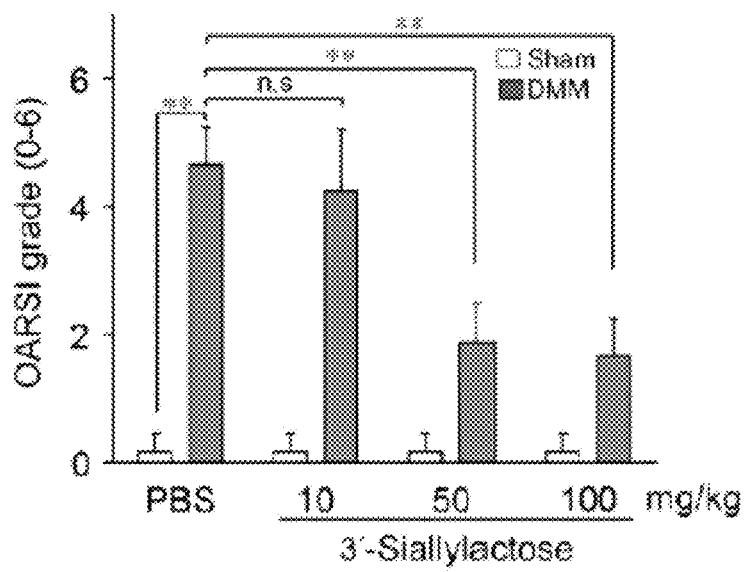
FIG. 9B is a graph showing cartilage destruction quantified by OARSI at 10 weeks following DMM surgery.

FIG. 9A shows photographs of Safranin-O staining of cartilage destruction in a DMM-induced osteoarthritis mouse model that had received gavage feeding of 3'-sialyllactose three times a week and a control mouse. FIG. 9B is a graph showing cartilage destruction quantified by OARSI at 10 weeks following DMM surgery.

As shown in FIG. 9B, DMM-induced osteoarthritis mouse model orally administered with 3'-sialyllactose showed remarkably low OARSI scores, as compared with control mouse, indicating significant inhibition of osteoarthritis development.

Figure 9C:
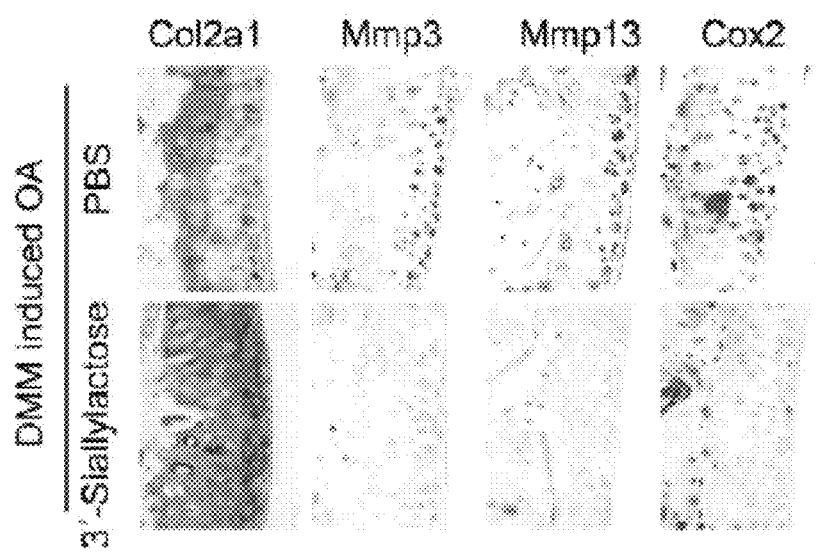
FIG. 9C shows photographs of immunohistochemical staining results of Col2α1, Mmp3, Mmp13 and Cox2 in a DMM-induced osteoarthritis mouse model orally administered with 3'-sialyllactose.
Figure 9D:
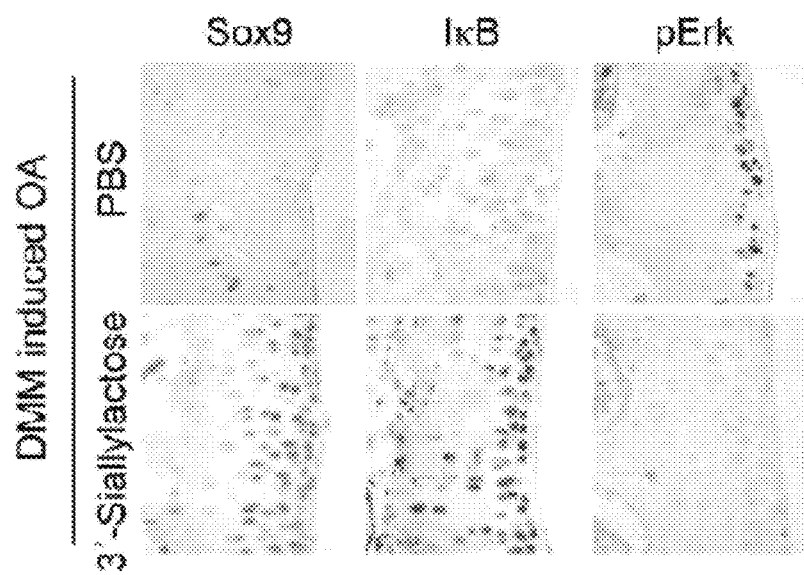
FIG. 9D shows photographs of immunohistochemical staining results of Sox9, IκB, and pErk.

FIG. 9C shows photographs of immunohistochemical staining results of Col2a1, Mmp3, Mmp13 and Cox2 in a DMM-induced osteoarthritis mouse model orally administered with 3'-sialyllactose, and FIG. 9D shows photographs of immunohistochemical staining results of Sox9, IκB, and pErk.

As shown in FIG. 9C, Mmp3, Mmp13, and Cox2 expression was decreased in an DMM-induced osteoarthritis mouse model orally administered with 3'-sialyllactose, but not decreased in the control mouse. That is, 3'-sialyllactose may inhibit cartilage destruction by catabolic factor in the DMM-induced osteoarthritis model.

6-3. Examination of Prophylactic and Therapeutic Effects of Sialyllactose in Rheumatoid Arthritis Model In order to examine prophylactic effects of 3'-sialyllactose during development of arthritis, collagen-induced arthritis (CIA) mouse model was orally administered with 3'-sialyllactose three times a week for 4 weeks at various concentrations (100 mg/kg and 500 mg/kg). In detail, the mouse models immunized day 1 and day 21 were orally administered with 3'-sialyllactose every other days for 4 weeks after second immunization. Control groups were orally administered with PBS, lactose, or sialic acid.

Next, in order to examine therapeutic effects of 3'-sialyllactose, mice with arthritis were orally administered with 3'-sialyllactose. In detail, 8-week-old DBA mice were immunized day 0 and day 21, and then orally administered with 500 mg/kg of 3'-sialyllactose every other days for 2 weeks. Control groups were administered with lactose (250 mg/kg), sialic acid (250 mg/kg), or MTX (1 mg/kg).

Figure 10A:
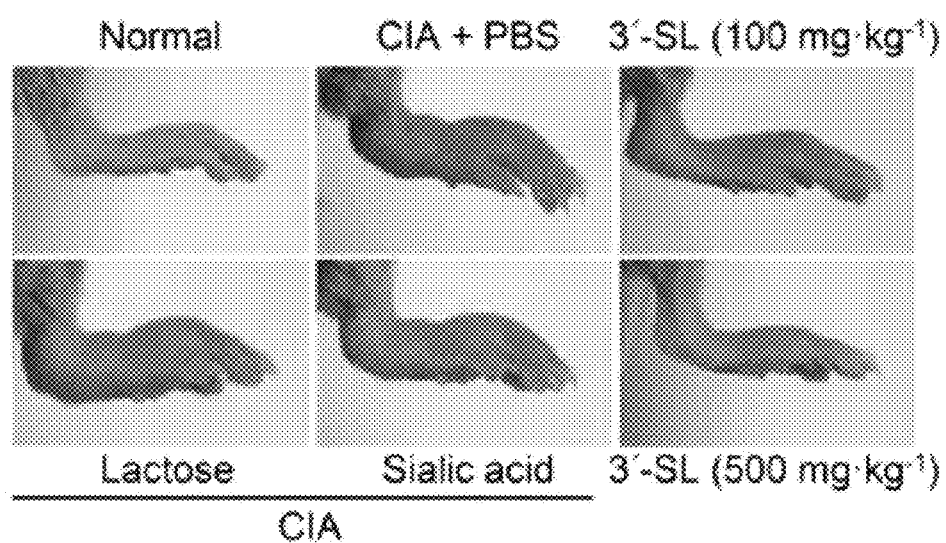
FIGS. 10A, 10B, 10C and 10D show prophylactic effects of 3'-sialyllactose in CIA mouse models.
Figure 10B:
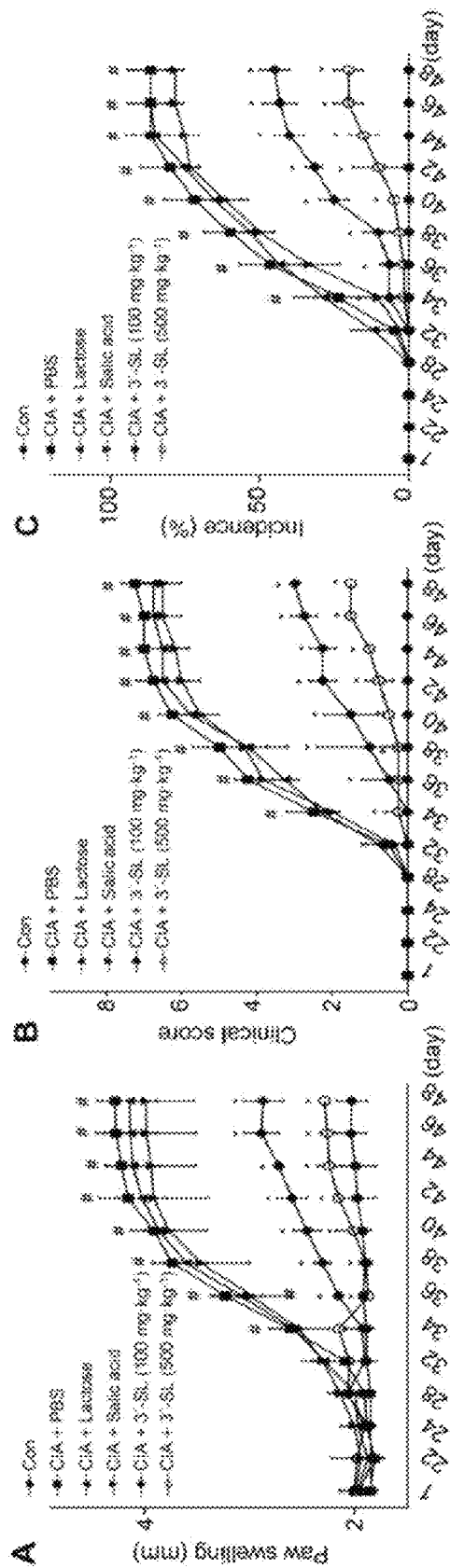
Figure 10C:
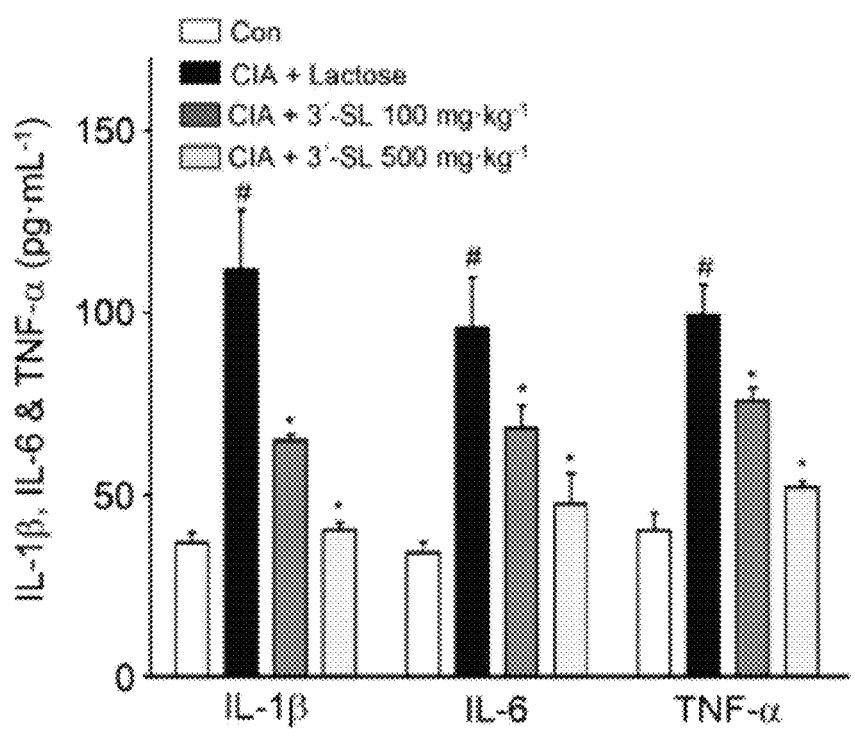
Figure 10D:
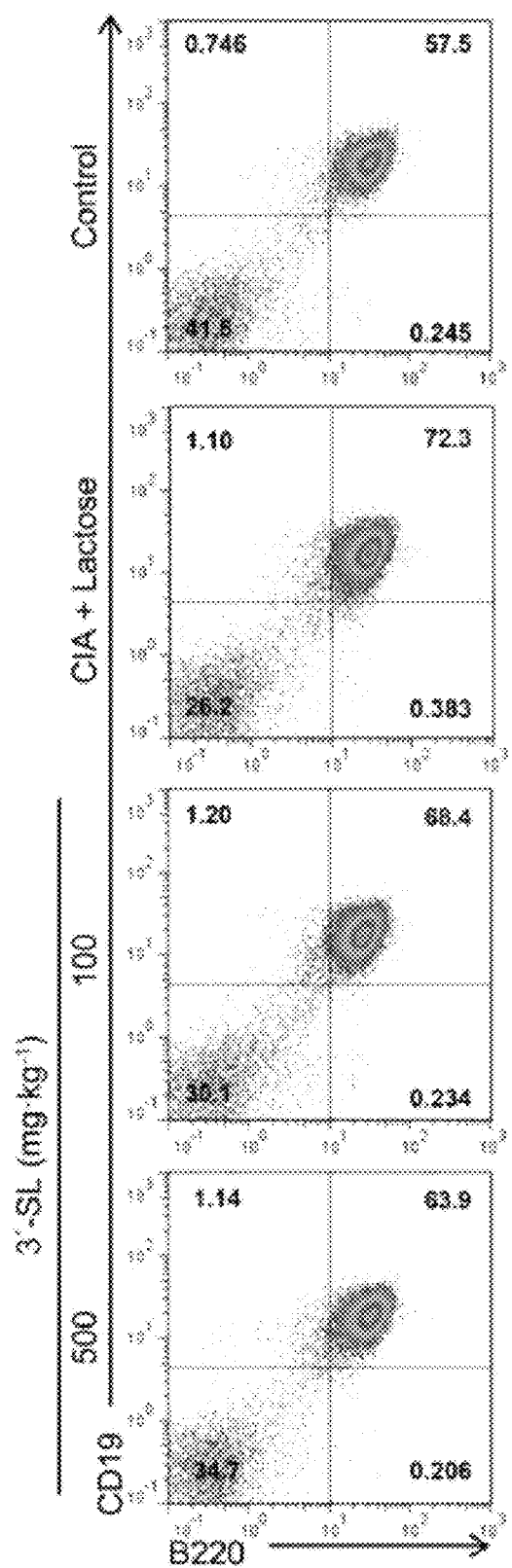

FIGS. 10A, 10B, 10C and 10D show prophylactic effects of 3'-sialyllactose in CIA mouse models. FIG. 10A shows a photograph of a hind paw of each treatment group at 4 weeks after arthritis induction, and FIG. 10B shows graphs illustrating hind paw swelling (A), clinical score (B), and incidence (C) of mice administered with PBS, lactose, sialic acid or 3'-sialyllactose. FIG. 10C is a graph showing production of pro-inflammatory cytokines in mouse sera at 48 days after administration of 3'-sialyllactose. FIG. 10D shows percentages of CD19$^+$B220$^+$ B cells in spleens of mice administered with lactose or 3'-sialyllactose.

As shown in FIGS. 10A, 10B, 10C and 10D, it was confirmed that 3'-sialyllactose alleviated swelling of CIA mouse model and decreased expression of pro-inflammatory cytokines, indicating prophylactic effects of 3'-sialyllactose on rheumatoid arthritis.

Figure 11A:
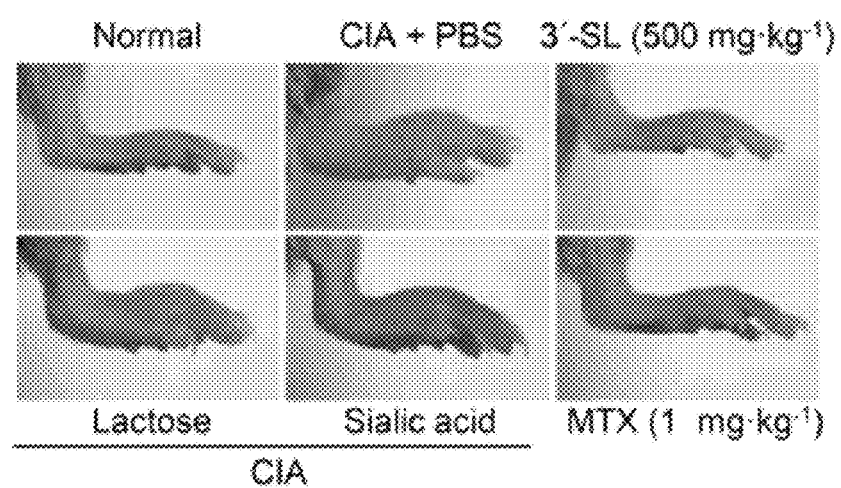
FIGS. 11A, 11B, 11C and 11D show therapeutic effects of 3'-sialyllactose in mouse models with arthritis.
Figure 11B:
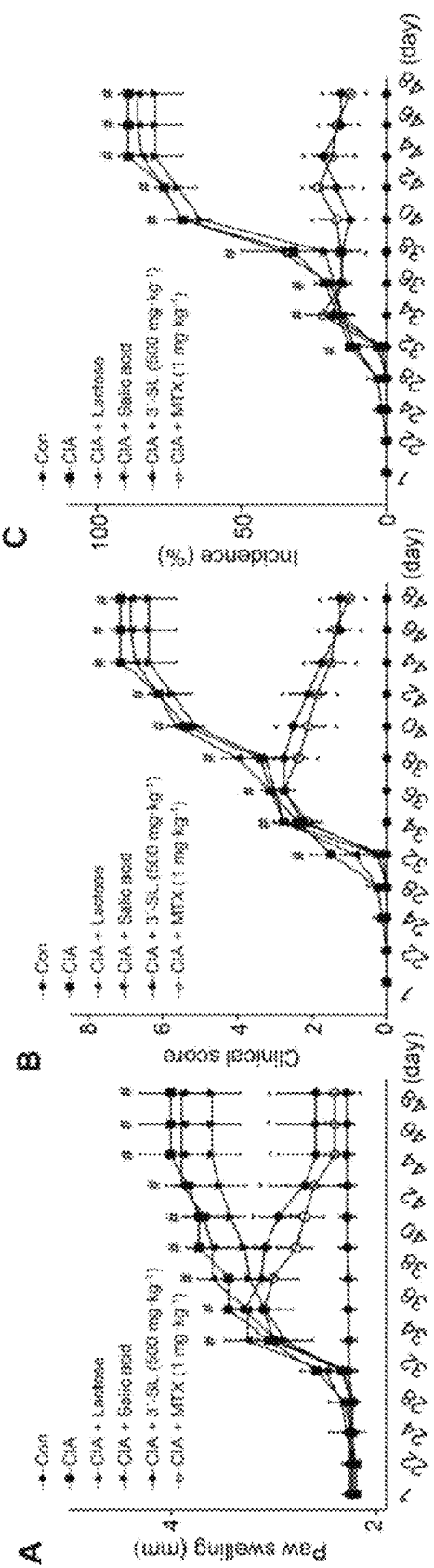
Figure 11C:
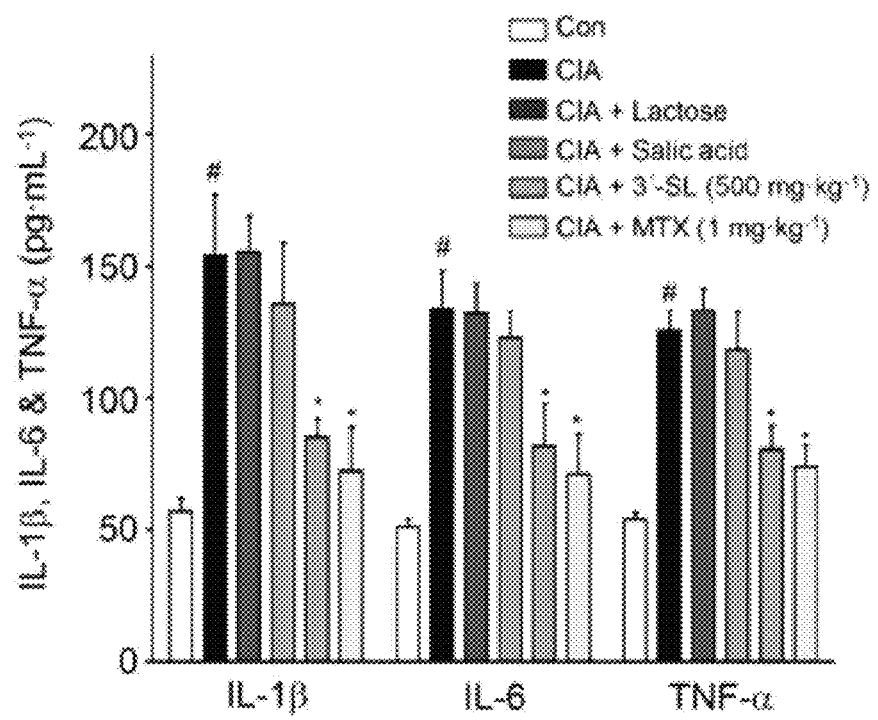
Figure 11D:
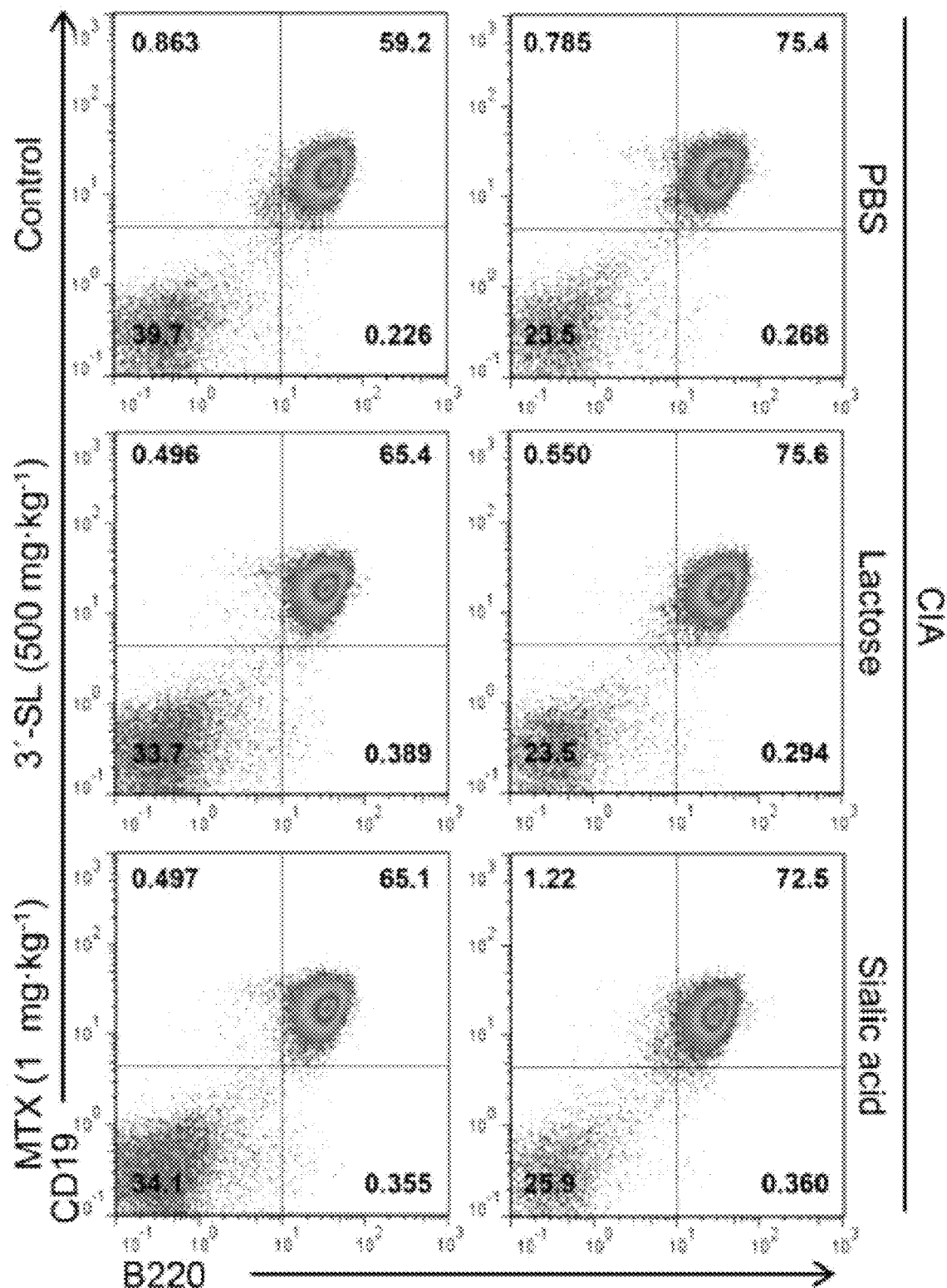

FIGS. 11A, 11B, 11C and 11D show therapeutic effects of 3'-sialyllactose in mouse models with arthritis. FIG. 11A shows a photograph of a hind paw of each treatment group at 4 weeks after arthritis induction, and FIG. 11B shows graphs illustrating hind paw swelling (A), clinical score (B), and incidence (C) of mice administered with lactose, sialic acid, MTX, or 3'-sialyllactose. FIG. 11C shows graphs illustrating production of pro-inflammatory cytokines in mouse sera at 48 days after administration of 3'-sialyllactose. FIG. 11D illustrates percentages of CD19$^+$B220$^+$ B cells in spleens of mice administered with lactose or 3'-sialyllactose.

As shown in FIGS. 11A, 11B, 11C and 11D, it was confirmed that 3'-sialyllactose alleviated swelling and decreased expression of pro-inflammatory cytokines in mouse models with rheumatoid arthritis, indicating therapeutic effects of 3'-sialyllactose on rheumatoid arthritis.

In other words, 3'-sialyllactose may exhibit prophylactic or therapeutic effects on rheumatoid arthritis by decreasing production of inflammatory cytokines.

Example 7. Examination of Regulation of Immune Cell Activity by 3'-Sialyllactose

7-1. Inhibition of Proliferation of FLS and Immune Cell

In order to examine protecting effects of 3'-sialyllactose during development of rheumatoid arthritis, mouse ankle and knee joints were stained with hematoxylin and Safranin-O.

Figure 12A:
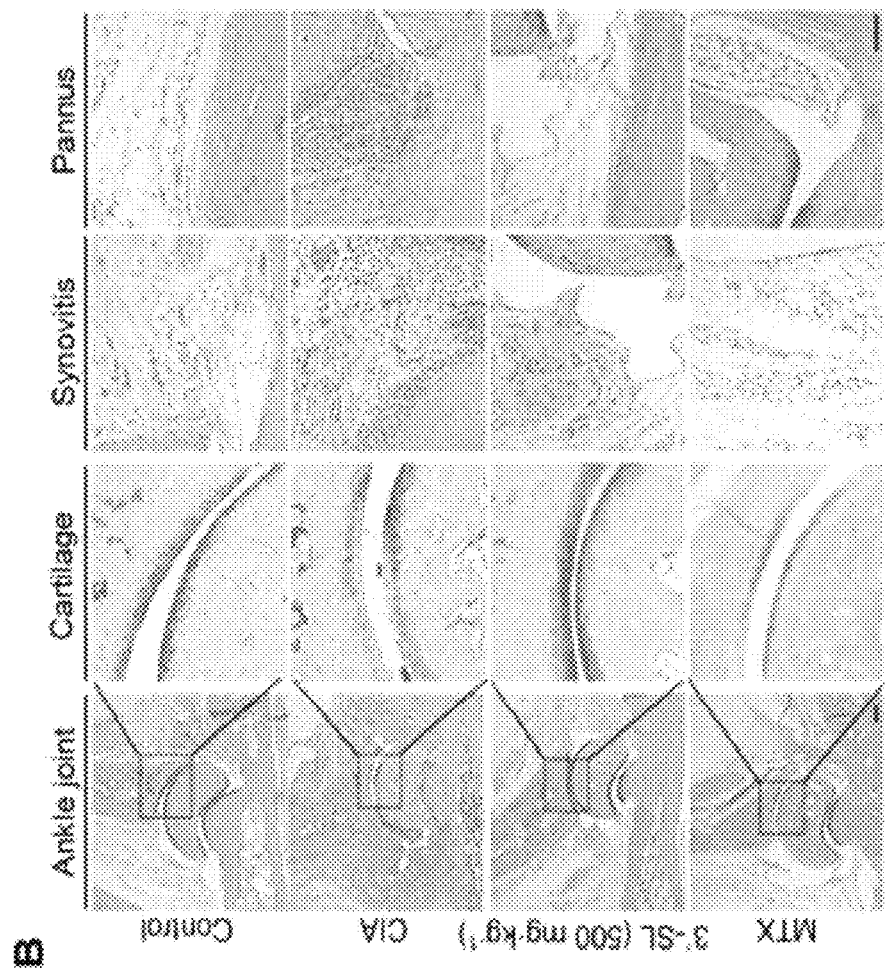
FIG. 12A shows photographs of hematoxylin and Safranin-O staining showing infiltration of mononuclear cells into the synovium of a mouse ankle joint (A), and infiltration of immune cells (B)
Figure 12B:
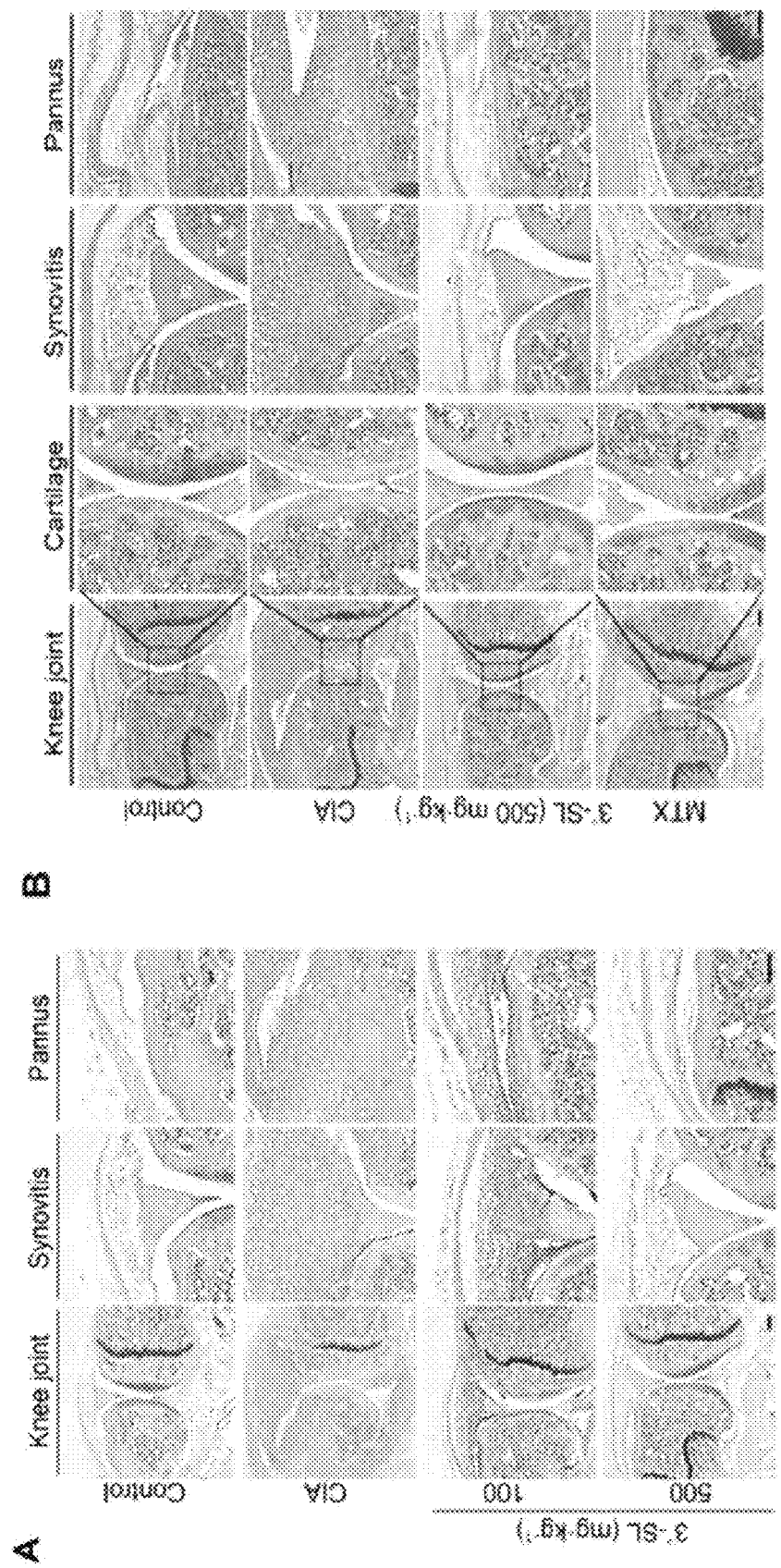
FIG. 12B shows photographs of hematoxylin and Safranin-O staining showing infiltration of mononuclear cells into the synovium of a mouse knee joint (A), and infiltration of immune cells (B)

FIG. 12A shows photographs of hematoxylin and Safranin-O staining showing infiltration of mononuclear cells into the synovium of a mouse ankle joint (A), and infiltration of immune cells (B), and FIG. 12B shows photographs of hematoxylin and Safranin-O staining showing infiltration of mononuclear cells into the synovium of a mouse knee joint (A), and infiltration of immune cells (B).

As shown in FIGS. 12A and 12B, it was confirmed that 3'-sialyllactose may inhibit synovial hyperplasia and infiltration of mononuclear cells into the ankle and knee joints.

Figure 13B:
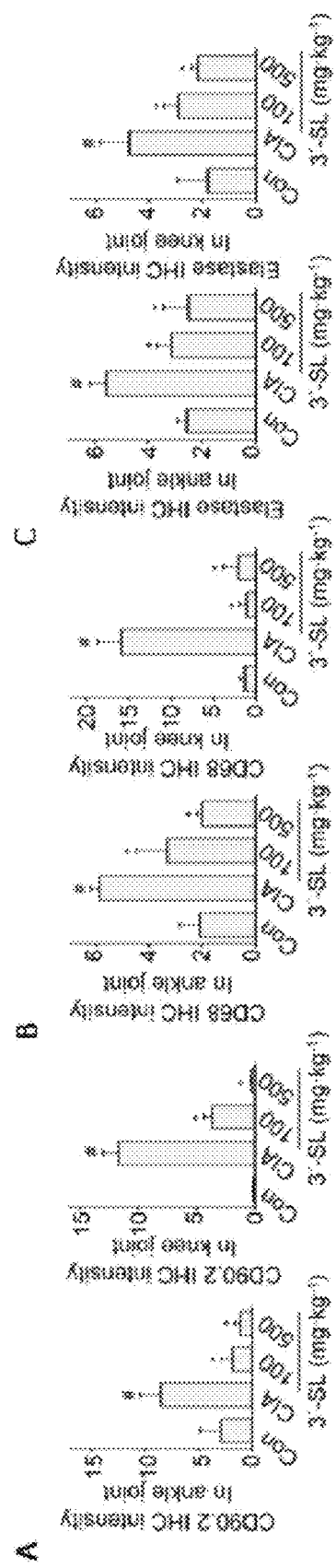
FIG. 13B shows graphs illustrating quantification of (A) FLS, (B) macrophages, and (C) neutrophils proliferated in the ankle (left) and knee (right) joints.

FIG. 13A shows photographs of (A) fibroblast-like synoviocytes (FLS), (B) macrophages, and (C) neutrophils proliferated in the synovial tissues of ankle and knee joints of a mouse, which were stained with anti-CD90.2, anti-CD68, and elastase, and FIG. 13B shows graphs illustrating quantification of (A) FLS, (B) macrophages, and (C) neutrophils proliferated in the ankle (left) and knee (right) joints.

As shown in FIGS. 13A and 13B, it was confirmed that proliferation of FSL, macrophages, and neutrophils by rheumatoid arthritis was significantly decreased by treatment with 3'-sialyllactose. In other words, 3'-sialyllactose may retard progression of rheumatoid arthritis and may decrease severity of rheumatoid arthritis by inhibiting FLS proliferation.

7-2. Reduction of Chemokine and Pro-Inflammatory Cytokine Expression

Anti-chemokine and anti-inflammatory effects of 3'-sialyllactose were examined. First, purity of mouse FLS was examined by FACS analysis, and then no effects of 3'-sialyllactose on FLS proliferation and cytotoxicity were examined by WST-1 assay (see FIGS. 14A-A to 14A-C). Further, in vitro analysis, as control groups for 3'-sialyllactose, sialic acid and lactose were used, and it was confirmed that there was no significant difference (see FIG. 14B). Therefore, in a subsequent in vitro experiment, 3'-sialyllactose was used at a concentration of 0 μM to 250 μM. In order to examine effects of 3'-sialyllactose on IL-1β-, IL-6-, IL-17-, and TNF-α-induced chemokines (e.g., CCL2, CCL5, CCL7, CXCL1, CXCL2, and CXCL5), pro-inflammatory cytokines (IL-1, IL-6, and TNF-α), and COX2 expression, IL-1β-, IL-6-, IL-17-, and TNF-α-stimulated human RA-FLS and mouse FLS were treated with 3'-sialyllactose (100 μM or 250 μM) for 24 hrs.

FIGS. 14A-A and 14A-B show FACS results of analyzing marker expression on the FLS surfaces in a mouse according to passages (FIG. 14A-A: CD90.2; FIG. 14A-B: CD14), and a graph of cytotoxicity confirmed by WST-1 assay (FIG. 14A-C), and FIG. 14B is a graph showing Mmp3, Mmp13, and COX2 expression levels according to lactose, sialic acid, and 3'-sialyllactose in IL-1β-treated mouse FLS.

Figure 15A:
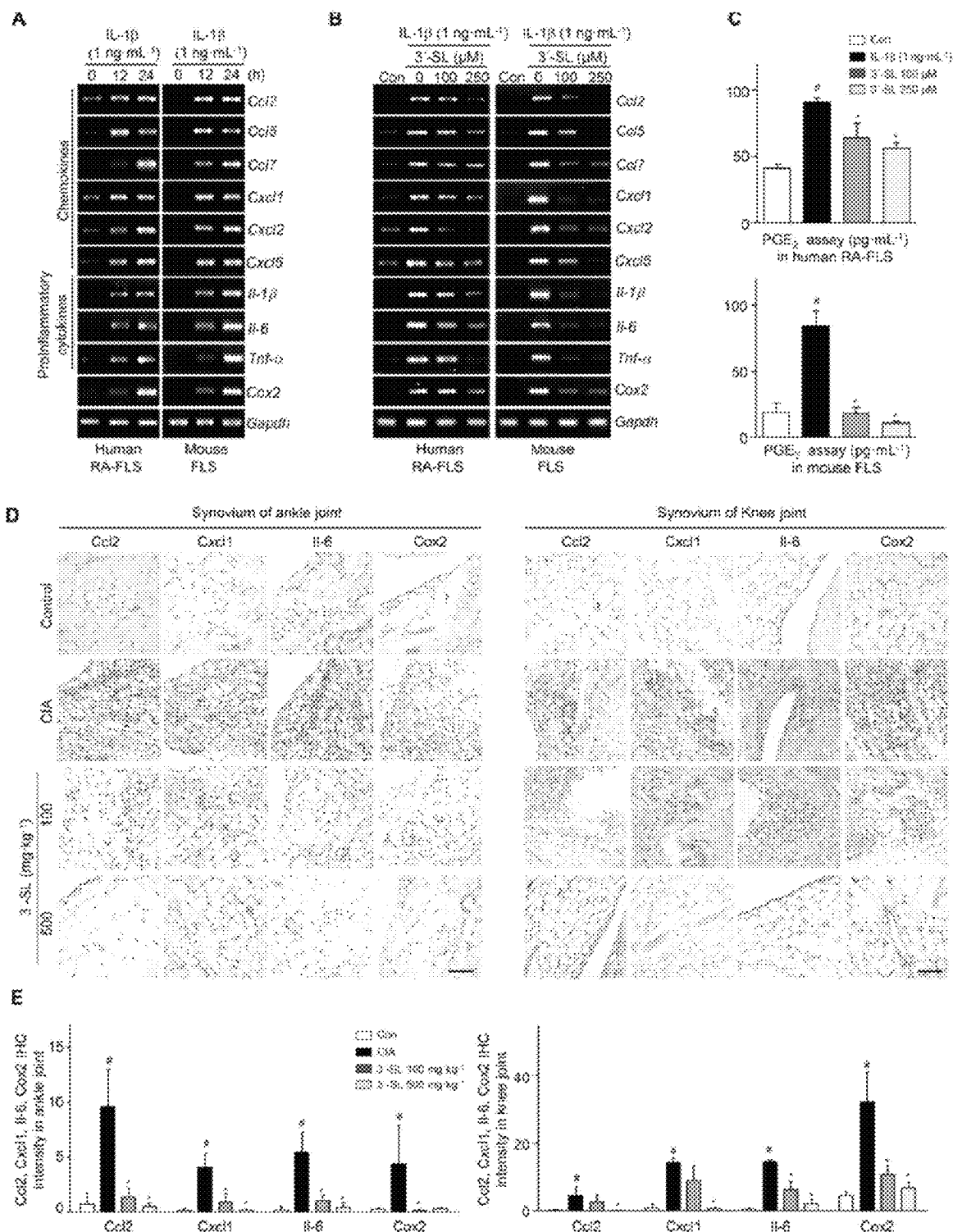
FIG. 15A shows expression of chemokines and pro-inflammatory cytokines by 3'-sialyllactose in human RA-FLS and mouse FLS; (A) shows expression of chemokines and pro-inflammatory cytokines at 0 hrs, 12 hrs, and 24 hrs after treatment of human RA-FLS and mouse FLS with 1 ng/mL of IL-1β, (B) shows expression of chemokines and pro-inflammatory cytokines at 24 hrs after treatment of human RA-FLS and mouse FLS with 1 ng/mL of IL-1β and 0 μM, 100 μM, and 250 μM of 3'-sialyllactose, (C) is a graph showing $PGE_2$ production after treatment of human RA-FLS and mouse FLS with IL-1β and 3'-sialyllactose, (D) shows immunohistochemical staining results of representative chemokines, pro-inflammatory cytokines, and COX2 in the synovial tissues of ankle (left) and knee (right) joints, and (E) is a graph showing quantification of CCL2, CXCL1, IL-6, and COX2 expression in the ankle (left) and knee (right) joints.

FIG. 15A shows expression of chemokines and pro-inflammatory cytokines by 3'-sialyllactose in human RA-FLS and mouse FLS. (A) shows expression of chemokines and pro-inflammatory cytokines at 0 hrs, 12 hrs, and 24 hrs after treatment of human RA-FLS and mouse FLS with 1 ng/mL of IL-1β. (B) shows expression of chemokines and pro-inflammatory cytokines at 24 hrs after treatment of human RA-FLS and mouse FLS with 1 ng/mL of IL-1β and 0 μM, 100 μM, and 250 μM of 3'-sialyllactose. (C) is a graph showing PGE$_2$ production after treatment of human RA-FLS and mouse FLS with IL-1β and 3'-sialyllactose. (D) shows immunohistochemical staining results of representative chemokines, pro-inflammatory cytokines, and COX2 in the synovial tissues of ankle (left) and knee (right) joints. (E) is a graph showing quantification of CCL2, CXCL1, IL-6, and COX2 expression in the ankle (left) and knee (right) joints.

FIGS. 15B-A to 15B-D show whether 3'-sialyllactose inhibited chemokines and pro-inflammatory cytokines which were increased by IL-1β, IL-6, IL-17, or TNF-α in human RA-FLS and mouse FLS.

As shown in FIGS. 15B-A to 15B-D, it was confirmed that 3'-sialyllactose remarkably decreased expression levels of chemokines, pro-inflammatory cytokines, and COX2 in IL-1β- (FIG. 15B-A), IL-6- (FIG. 15B-B), IL-17- (FIG. 15B-C), and TNF-α (FIG. 15B-D)-stimulated human RA-FLS and mouse FLS. In other words, 3'-sialyllactose may decrease production of chemokines, inflammatory cytokines, and inflammatory mediators which are secreted by IL-1β-, IL-6-, IL-17-, and TNF-α-stimulated FLS.

Example 8. Examination of Inhibition of Atopic Dermatitis by Sialyllactose

In order to examine inhibitory effect of 3'-sialyllactose on atopic dermatitis, ear thickness of atopic dermatitis mouse model was examined at 28 days after oral administration of 100 mg/kg or 500 mg/kg of 3'-sialyllactose. Further, the left ear skin of the mouse was cut into thin sections, stained with hematoxylin and eosin (H&E), and stained with toluidine blue.

Figure 16A:
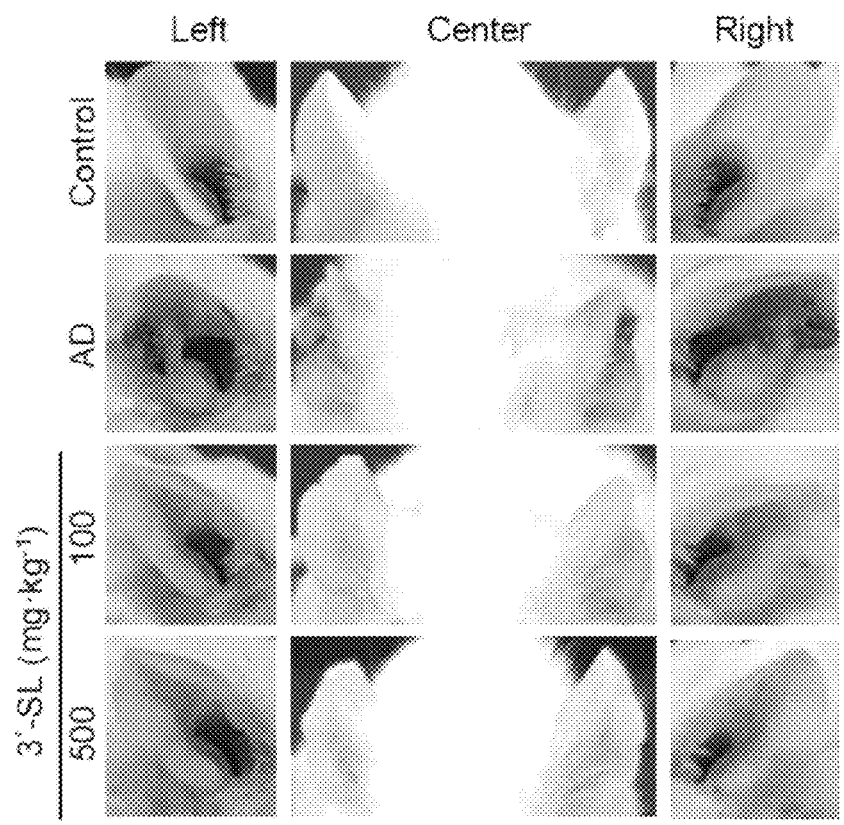
FIG. 16A shows photographs illustrating changes in the ear thickness of an atopic dermatitis mouse model before and 28 days after oral administration of 3'-sialyllactose.
Figure 16B:
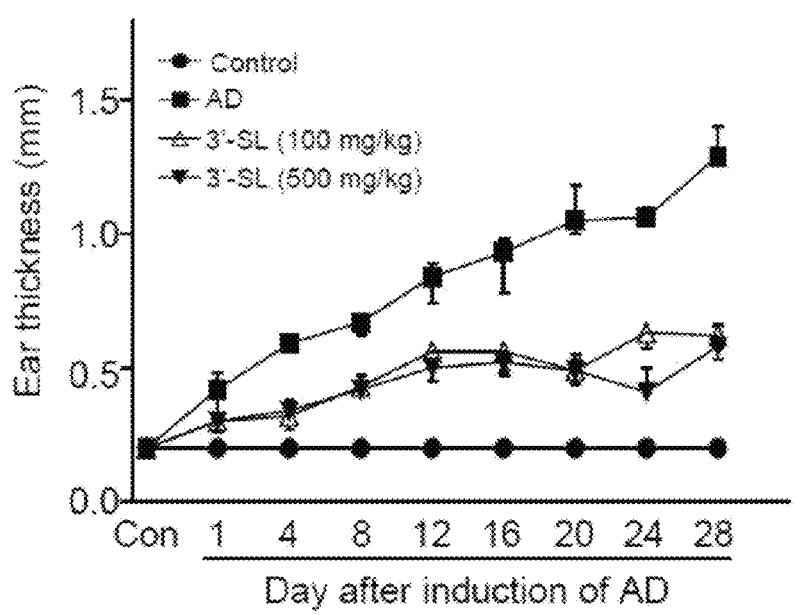
FIG. 16B is a graph showing changes in the ear thickness of an atopic dermatitis mouse model.

FIG. 16A shows photographs illustrating changes in the ear thickness of an atopic dermatitis mouse model before and 28 days after oral administration of 3'-sialyllactose, FIG. 16B is a graph showing changes in the ear thickness of an atopic dermatitis mouse model.

As shown in FIGS. 16A and 16B, it was confirmed that the mouse ear thickness was decreased after oral administration of the atopic dermatitis mouse model with 3'-sialyllactose. In other words, 3'-sialyllactose may decrease skin thickness by alleviating inflammation of atopic dermatitis.

Figure 16C:
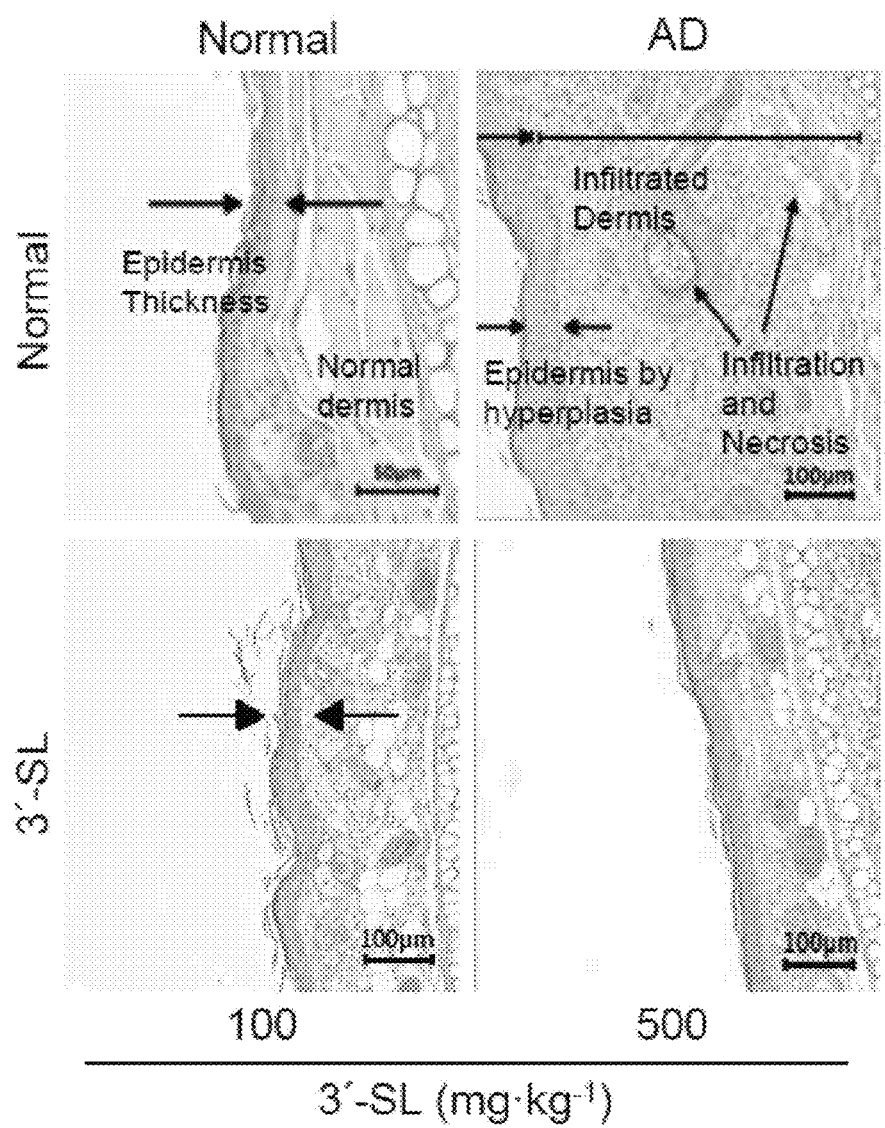
FIG. 16C shows microscopic images of the ear skin of an atopic dermatitis mouse model after H&E staining.
Figure 16D:
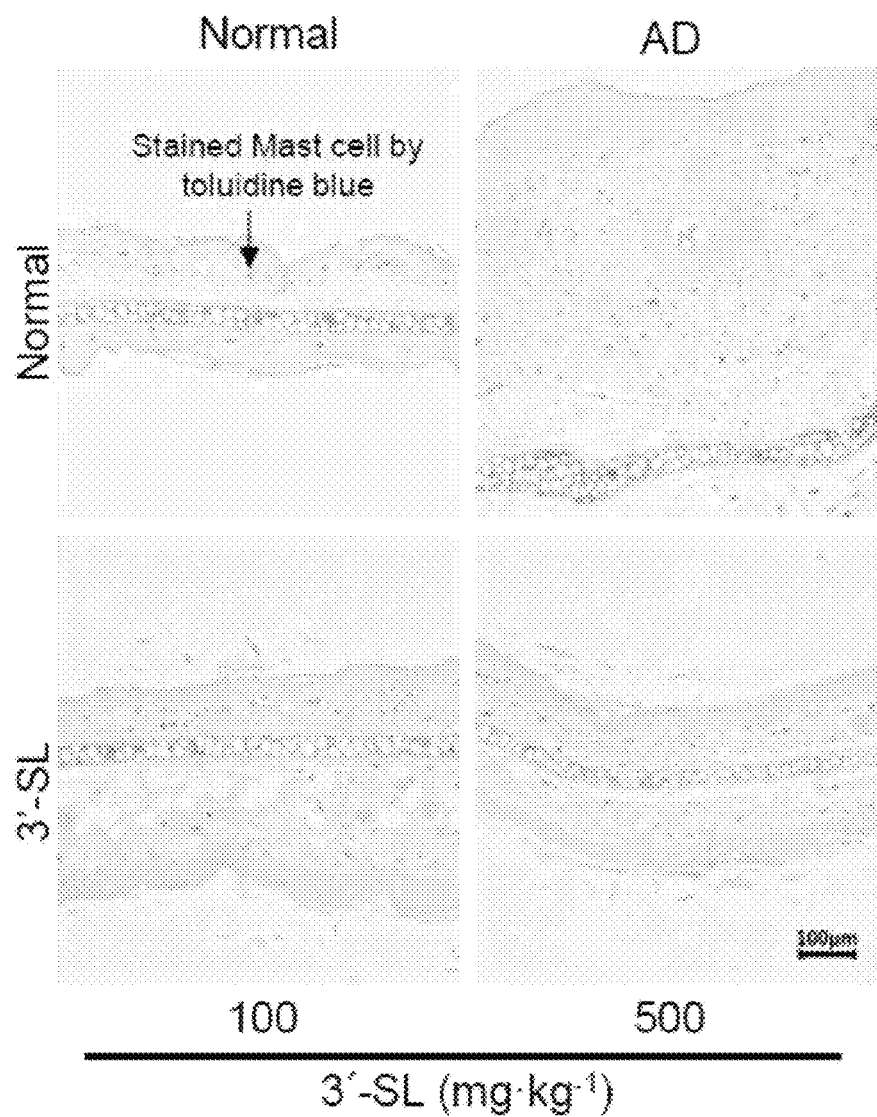
FIG. 16D shows microscopic images thereof after toluidine blue staining.

FIG. 16C shows microscopic images of the ear skin of an atopic dermatitis mouse model after H&E staining, and FIG. 16D shows microscopic images thereof after toluidine blue staining.

Figure 16E:
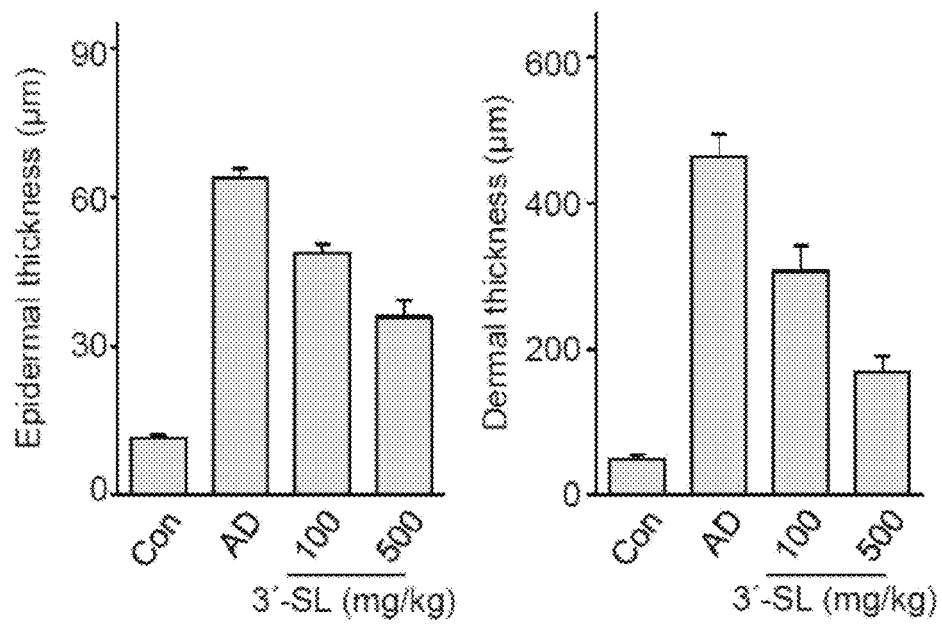
FIG. 16E shows graphs showing ear epidermal and dermal thickness of an atopic dermatitis mouse model.

FIG. 16E shows graphs showing ear epidermal and dermal thickness of an atopic dermatitis mouse model.

As shown in FIG. 16E, it was confirmed that ear epidermal and dermal thickness of atopic dermatitis mouse model were decreased after oral administration of 3'-sialyllactose, and they were decreased in a concentration-dependent manner.

Figure 16F:
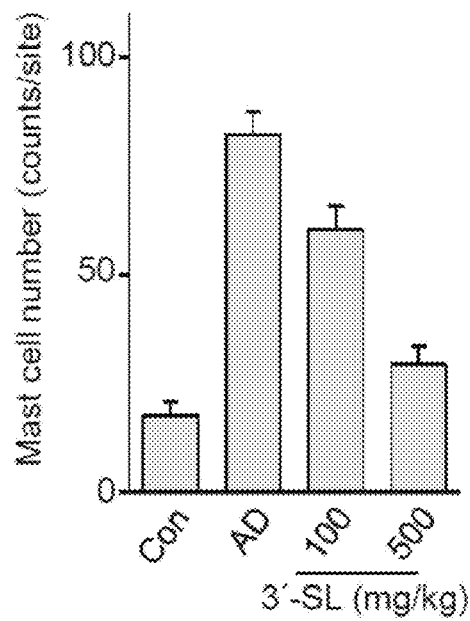
FIG. 16F is a graph showing the number of mast cells in the ear skin which was examined by toluidine blue staining.

FIG. 16F is a graph showing the number of mast cells in the ear skin which was examined by toluidine blue staining.

As shown in FIG. 16F, it was confirmed that the number of mast cells was decreased in a 3'-sialyllactose concentration-dependent manner. In other words, 3'-sialyllactose may decrease an allergic reaction in atopic dermatitis by decreasing the number of mast cells.

Statistical Analysis

All results of Examples of the present disclosure were analyzed by the nonparametric statistical method using data based on ordinal grading systems, such as Mankin scores. qRT-PCR data presented as the fold change were initially tested for conformation to a normal distribution using the Shapiro-Wilk test, then analyzed by Student's t-test and analysis of variance (ANOVA) with post hoc tests each for pair-wise comparisons and multi-comparisons as appropriate. Significance was accepted at the 0.05 level of probability ($P<0.05$).

INDUSTRIAL APPLICABILITY

3'- or 6'-sialyllactose of the present disclosure may promote cartilage formation and may effectively inhibit cartilage destruction at the same time, and therefore, it may be useful as a composition for preventing or treating osteoarthritis.

The above described exemplary embodiments of the present disclosure have been described for illustrative purposes, and it will be understood by those skilled in the art that the present disclosure may be implemented in a different specific form without changing the technical spirit or essential characteristics thereof. Therefore, it should be understood that the above embodiment is not limitative, but illustrative in all aspects.

The invention claimed is:

1. A method of inhibiting immune cell proliferation, the method comprising administering a therapeutically effective amount of a composition containing sialyllactose or a pharmaceutically acceptable salt thereof as an active ingredient to a patient in need thereof,
wherein the effective amount is determined by increased expression of type II collagen (Col2a1), increased Sox-9 activity, and/or decreased expression of matrix metalloproteinase3 (Mmp3) or matrix metalloproteinase13 (Mmp13).

2. The method of claim 1, wherein the sialyllactose is 3'-sialyllactose or 6'-sialyllactose.

3. The method of claim 2, wherein the salt of 3'-sialyllactose has a structure of the following Formula 1:

[Formula 1]

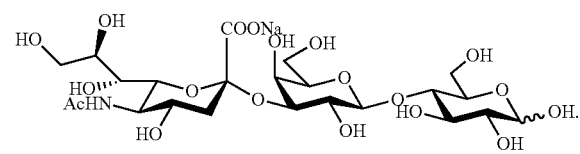

4. The method of claim 2, wherein the salt of 6'-sialyllactose has a structure of the following Formula 2:

[Formula 2]

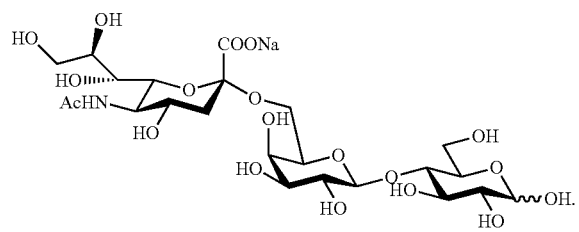

5. The method of claim 1, wherein the method has therapeutic effects on atopic dermatitis or rheumatoid arthritis.

6. The method of claim 1, wherein the method has one or more of the following characteristics of:
1) Decreasing expression of chemokines;
2) Decreasing expression of pro-inflammatory cytokines;
3) Decreasing production of inflammatory mediators;
4) Decreasing expression of COX2; and
5) Decreasing production of prostaglandin E2 ($PGE_2$).

7. The method of claim 1, wherein the method has one or more of the following characteristics of:
1) Inhibiting synovial hyperplasia; and
2) Inhibiting infiltration of mononuclear cells.

8. The method of claim 1, wherein the composition further contains a pharmaceutically acceptable carrier, excipient, or diluent.

9. A method of promoting cartilage formation or inhibiting cartilage destruction on rheumatoid arthritis, the method comprising administering a therapeutically effective amount of a composition containing sialyllactose or a pharmaceutically acceptable salt thereof as an active ingredient to a patient in need thereof,
wherein the effective amount is determined by increased expression of type II collagen (Col2a1), increased Sox-9 activity, and/or decreased expression of matrix metalloproteinase3 (Mmp3) or matrix metalloproteinase13 (Mmp13).

10. The method of claim 9, wherein the sialyllactose is 3'-sialyllactose or 6'-sialyllactose.

11. The method of claim 10, wherein the salt of 3'-sialyllactose has a structure of the following Formula 1:

[Formula 1]

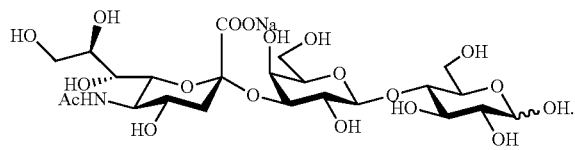

12. The method of claim 10, wherein the salt of 6'-sialyllactose has a structure of the following Formula 2:

[Formula 2]

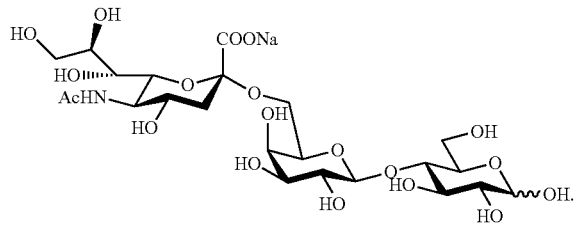

13. A method of treating atopic dermatitis, the method comprising administering a therapeutically effective amount of a composition containing sialyllactose or a pharmaceutically acceptable salt thereof as an active ingredient to a patient in need thereof,
wherein the effective amount is determined by increased expression of type II collagen (Col2a1), increased Sox-9 activity, and/or decreased expression of matrix metalloproteinase3 (Mmp3) or matrix metalloproteinase13 (Mmp13).

14. The method of claim 13, wherein the sialyllactose is 3'-sialyllactose or 6'-sialyllactose.

15. The method of claim 14, wherein the salt of 3'-sialyllactose has a structure of the following Formula 1:

[Formula 1]

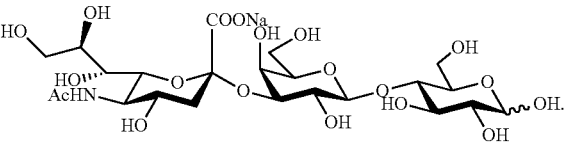

16. The method of claim 14, wherein the salt of 6'-sialyllactose has a stricture of the following Formula 2:

[Formula 2]

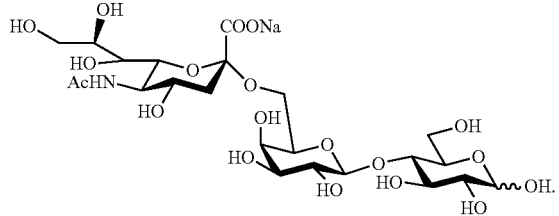

17. The method of claim 13, wherein the method has one or more of the following characteristics of:
1) Decreasing skin epidermal thickness;
2) Decreasing skin dermal thickness; and
3) decreasing the number of mast cells.

* * * * *